US010808946B2

(12) United States Patent
Baker et al.

(10) Patent No.: US 10,808,946 B2
(45) Date of Patent: Oct. 20, 2020

(54) INSULATED CHAMBER WITH PHASE CHANGE MATERIAL AND DOOR WITH CONTROLLABLE TRANSPARENCY

(71) Applicant: CARON PRODUCTS AND SERVICES, INC., Marietta, OH (US)

(72) Inventors: Milton Baker, Vincent, OH (US); Dale Barnett, Marietta, OH (US); Robert Dotterer, Sardis, OH (US); David Figel, Caldwell, OH (US); Stephen C. Keiser, Vienna, WV (US)

( * ) Notice: Subject to any disclaimer, the term of this patent is extended or adjusted under 35 U.S.C. 154(b) by 331 days.

(21) Appl. No.: 15/747,020

(22) PCT Filed: Jun. 15, 2016

(86) PCT No.: PCT/US2016/037707
§ 371 (c)(1),
(2) Date: Jan. 23, 2018

(87) PCT Pub. No.: WO2017/014873
PCT Pub. Date: Jan. 26, 2017

(65) Prior Publication Data
US 2018/0216833 A1    Aug. 2, 2018

Related U.S. Application Data

(60) Provisional application No. 62/195,960, filed on Jul. 23, 2015.

(51) Int. Cl.
*F24C 15/34* (2006.01)
*F24C 15/04* (2006.01)
(Continued)

(52) U.S. Cl.
CPC ............ *F24C 15/34* (2013.01); *A01K 41/023* (2013.01); *C12M 23/22* (2013.01); *C12M 41/14* (2013.01);
(Continued)

(58) Field of Classification Search
CPC ...... F24C 15/34; A01K 41/023; C12M 23/22; C12M 41/14
(Continued)

(56) References Cited

U.S. PATENT DOCUMENTS

| 4,701,415 A | 10/1987 | Dutton |
| 4,936,377 A | 6/1990 | DeVogel |

(Continued)

FOREIGN PATENT DOCUMENTS

| CA | 2838671 | 1/2012 |
| DE | 102004035017 | 2/2006 |

(Continued)

OTHER PUBLICATIONS

PCT/US2016/37707 International Search Report.

*Primary Examiner* — Vishal Pancholi
(74) *Attorney, Agent, or Firm* — Wolter Van Dyke Davis, PLLC; John L. DeAngelis

(57) ABSTRACT

A hinged door for gaining access to a chamber interior region for receiving a storage item therein. The hinged door comprising a frame, a transparent material pane within the frame, a smart glass material disposed proximate the material pane and controllable between a transparent and opaque condition responsive to an electric current supplied to the smart glass material, a phase change material within the frame, and a temperature controlling device proximate the phase change material.

18 Claims, 19 Drawing Sheets

(51) Int. Cl.
  *A01K 41/02* (2006.01)
  *C12M 1/00* (2006.01)
  *F24C 7/08* (2006.01)
  *F24C 15/02* (2006.01)
  *A01K 61/17* (2017.01)

(52) U.S. Cl.
  CPC ............... *F24C 7/08* (2013.01); *F24C 15/02* (2013.01); *F24C 15/04* (2013.01); *A01K 61/17* (2017.01)

(58) Field of Classification Search
  USPC .......................................................... 219/399
  See application file for complete search history.

(56) References Cited

U.S. PATENT DOCUMENTS

| | | |
|---|---|---|
| 4,951,481 A | 8/1990 | Negishi |
| 5,899,088 A | 5/1999 | Purdum |
| 5,950,450 A | 9/1999 | Meyer |
| 6,001,487 A | 12/1999 | Ladang |
| 6,294,298 B1 | 9/2001 | Gentile |
| 6,308,518 B1 | 10/2001 | Hunter |
| 6,320,164 B2 | 11/2001 | Millett |
| 7,422,143 B2 | 9/2008 | Mayer |
| 7,516,600 B1 | 4/2009 | Flora |
| 7,913,511 B2 | 3/2011 | Meyer |
| 8,651,391 B2 | 2/2014 | Patch |
| 2004/0231355 A1 | 11/2004 | Mayer |
| 2005/0279730 A1 | 12/2005 | Miyake |
| 2007/0186580 A1 | 8/2007 | Kaplan |
| 2008/0197139 A1 | 8/2008 | Goncharko |
| 2009/0039088 A1 | 2/2009 | Williams |
| 2009/0305397 A1 | 12/2009 | Dodgson |
| 2010/0024439 A1 | 2/2010 | Finke |
| 2011/0315783 A1 | 12/2011 | Baker |

FOREIGN PATENT DOCUMENTS

| | | |
|---|---|---|
| DE | 202006010757 | 11/2006 |
| EP | 1901054 | 3/2008 |
| EP | 2000529 | 12/2008 |
| GB | 1338553 | 11/1973 |
| WO | 9519533 | 7/1995 |
| WO | 2006008276 | 1/2006 |

INSULATED CHAMBER WITH PHASE CHANGE MATERIAL AND DOOR WITH CONTROLLABLE TRANSPARENCY

CROSS REFERENCE TO RELATED APPLICATIONS

This national stage application claims priority to PCT Application No. PCT/US2016/37707, filed on Jun. 15, 2016, which claims the benefit of U.S. provisional patent application filed on Jul. 23, 2015 and assigned Application No. 62/195,960. Both of which are incorporated herein in their entirety.

FIELD OF THE INVENTION

The present invention relates generally to insulated chambers such as incubators, environmental chambers, freezers, refrigerators and ovens. More particularly, the present invention relates to an insulated chamber comprising a phase change material for enhancing temperature control and a door with controllable transparency.

BACKGROUND OF THE INVENTION

Insulated chambers may be used for a variety of purposes. For instance, such chambers may include incubators, environmental chambers, freezers, refrigerators and ovens. Incubators are typically used for growing cultures in a controlled environment, wherein temperature, humidity, and atmospheric gas concentration are maintained at selected levels. For certain applications it is highly desirable to have both temperature and gas concentrations maintained within strict tolerances while still allowing easy access to the incubator chamber for adding or removing items to and from the chamber or for inspecting the contents of the chamber. Control of environmental variables is desirable to maintain accuracy and reproducibility of incubation results.

Typical incubators have used either open-coil heaters within the incubator chamber or water jackets surrounding the incubator chamber. However, while such configurations can be effective in heating an incubator, they do not necessarily provide as strict a control on the incubator temperature as is desirable for consistent results.

Conventional air heater type incubators lack the temperature stability of the water jacket type. Water-jacketed incubators maintain temperature by surrounding the interior chamber with heated water in a separate compartment. The water is heated and circulates around the inner chamber via natural convection. The heat from the water radiates to the interior chamber to maintain a substantially constant temperature inside. Water is an effective thermal insulator and the water-jacket system is considered a more reliable method of heating in case of a power outage. In the wake of a power failure, a water-jacketed incubator will hold a set temperature inside the chamber 4-5 times longer than a radiant-walled unit.

Radiant-walled incubators heat the interior chamber using heaters mounted in the surrounding cavity that radiate heat through to the inside chamber. A radiant-walled heating system allows for quick recovery of temperature following door openings or changes in temperature settings. Radiant-walled heating systems are also more simplified for the user, not requiring filling, monitoring, and emptying water in the water jacket.

A fan may be mounted outside of the culturing area to help to circulate the air inside the chamber without disturbing cultures. This gentle circulation helps maintain a consistent temperature throughout the chamber and speeds recovery of internal temperature as well as $CO_2$ and humidity levels following door openings.

BRIEF DESCRIPTION OF THE FIGURES

A preferred embodiment of the invention, illustrated of the best mode in which Applicant contemplates applying the principles, is set forth in the following description and is shown in the drawings and is particularly and distinctly pointed out and set forth in the appended claims.

Similar numbers refer to similar parts throughout the drawings.

DETAILED DESCRIPTION OF THE INVENTION

Figure 1:
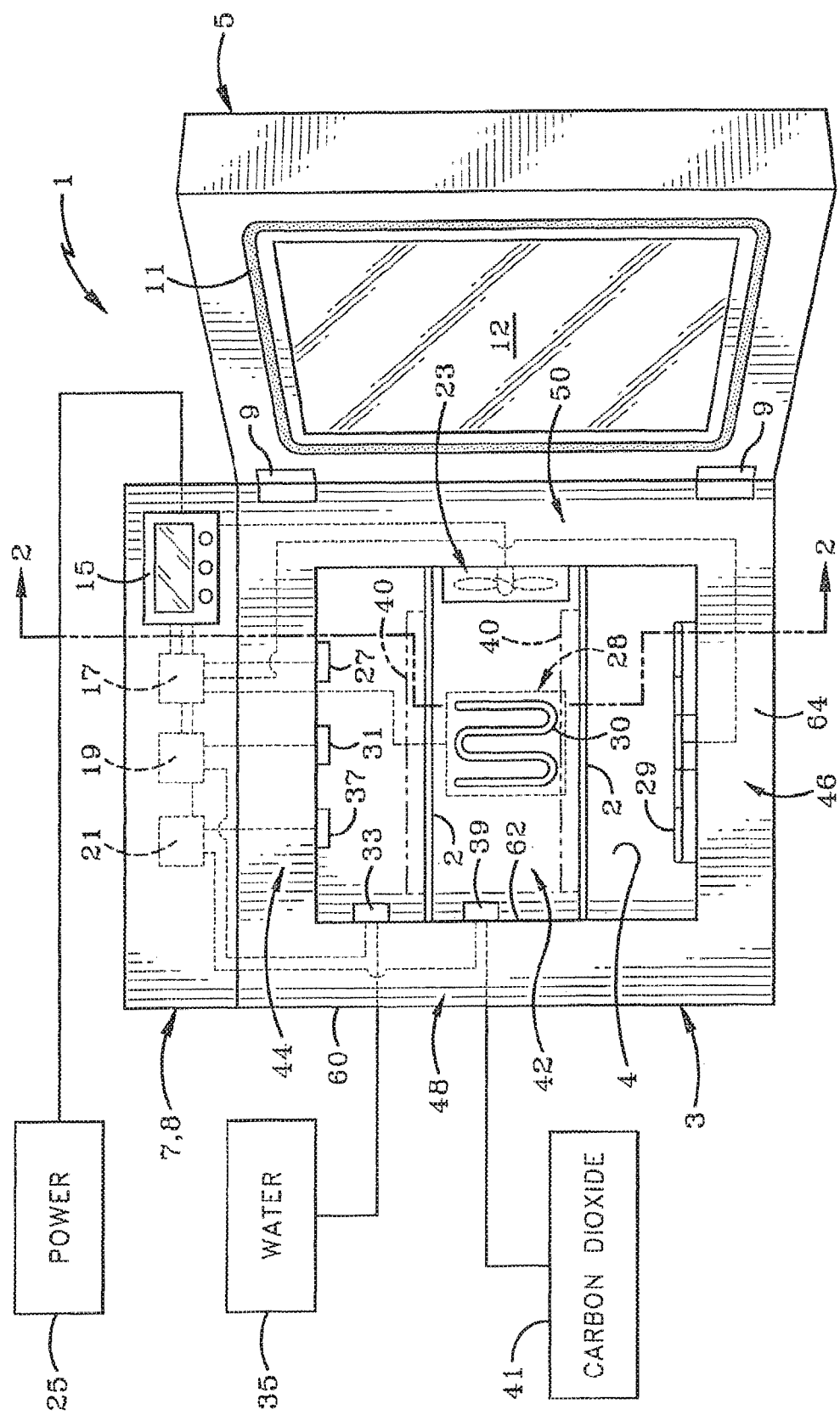
FIG. 1 is a front elevational view of a first embodiment of the insulated chamber of the present invention with portions shown diagrammatically.
Figure 4:
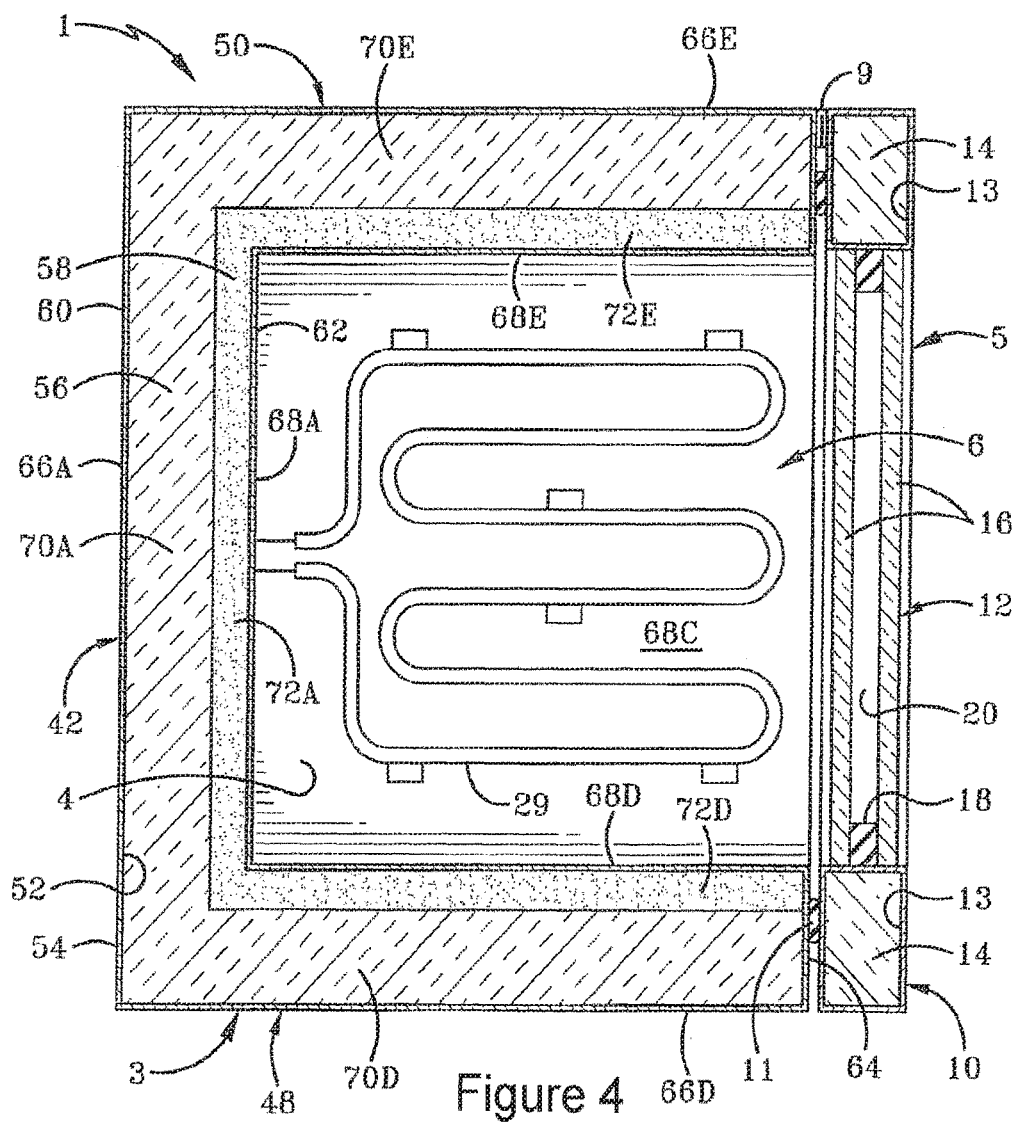
FIG. 4 is a sectional view taken on Line 4-4 of FIG. 2.
Figure 5:
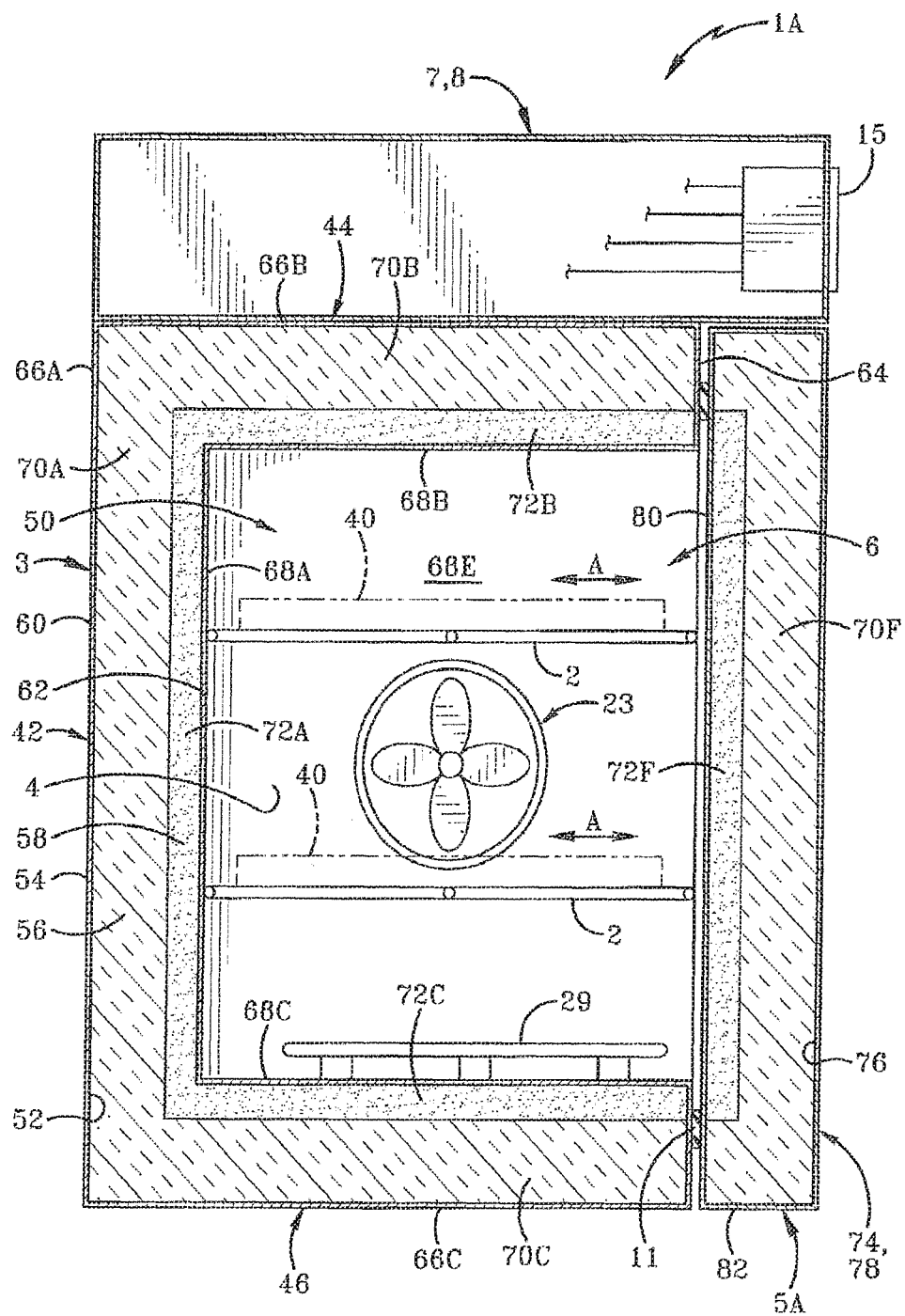
FIG. 5 is similar to FIG. 2 and is a sectional view of a second embodiment of the chamber of the present invention.
Figure 7:
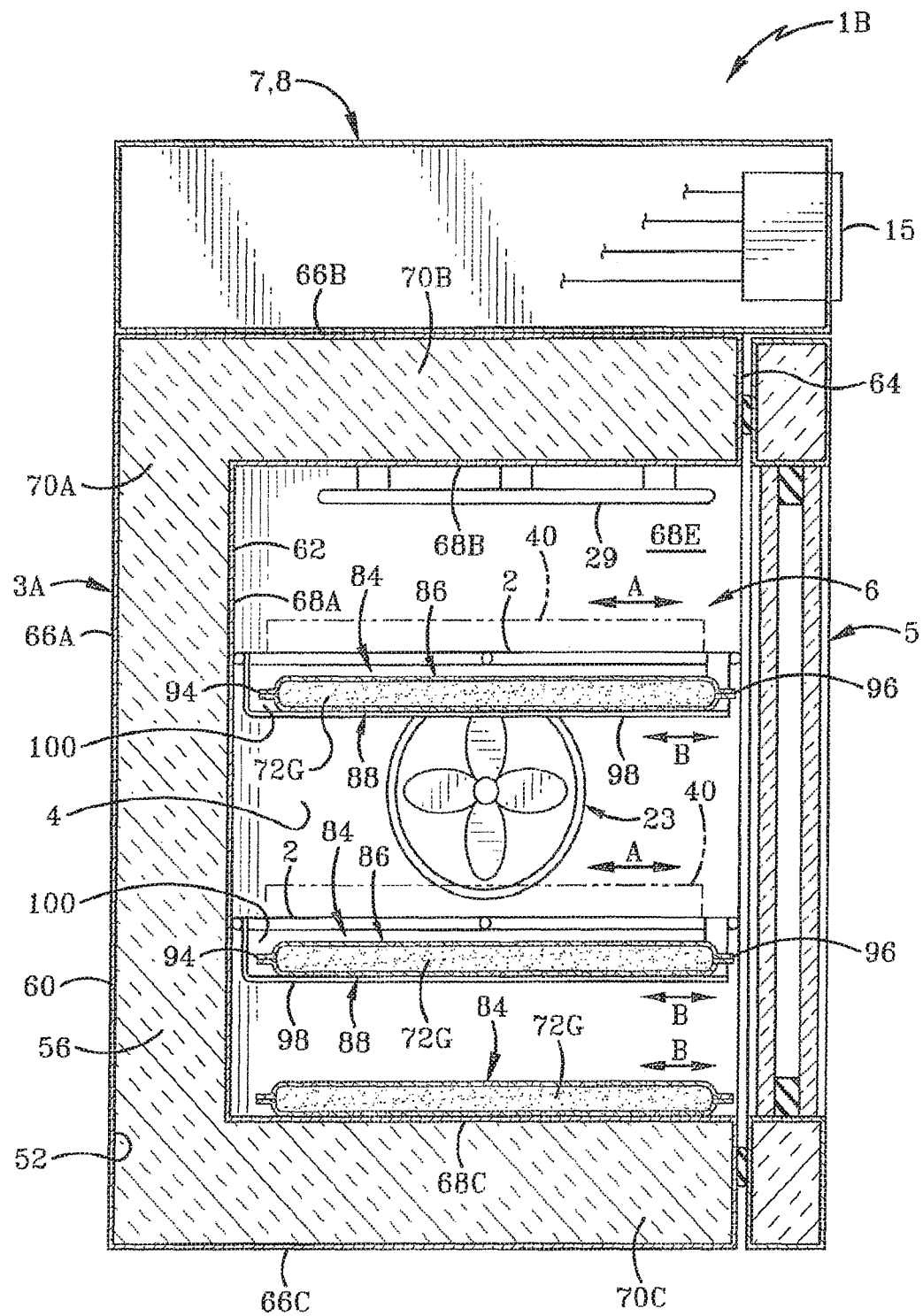
FIG. 7 is a sectional view similar to FIG. 2 of a third embodiment of the chamber of the present invention utilizing the phase change material packets.
Figure 8:
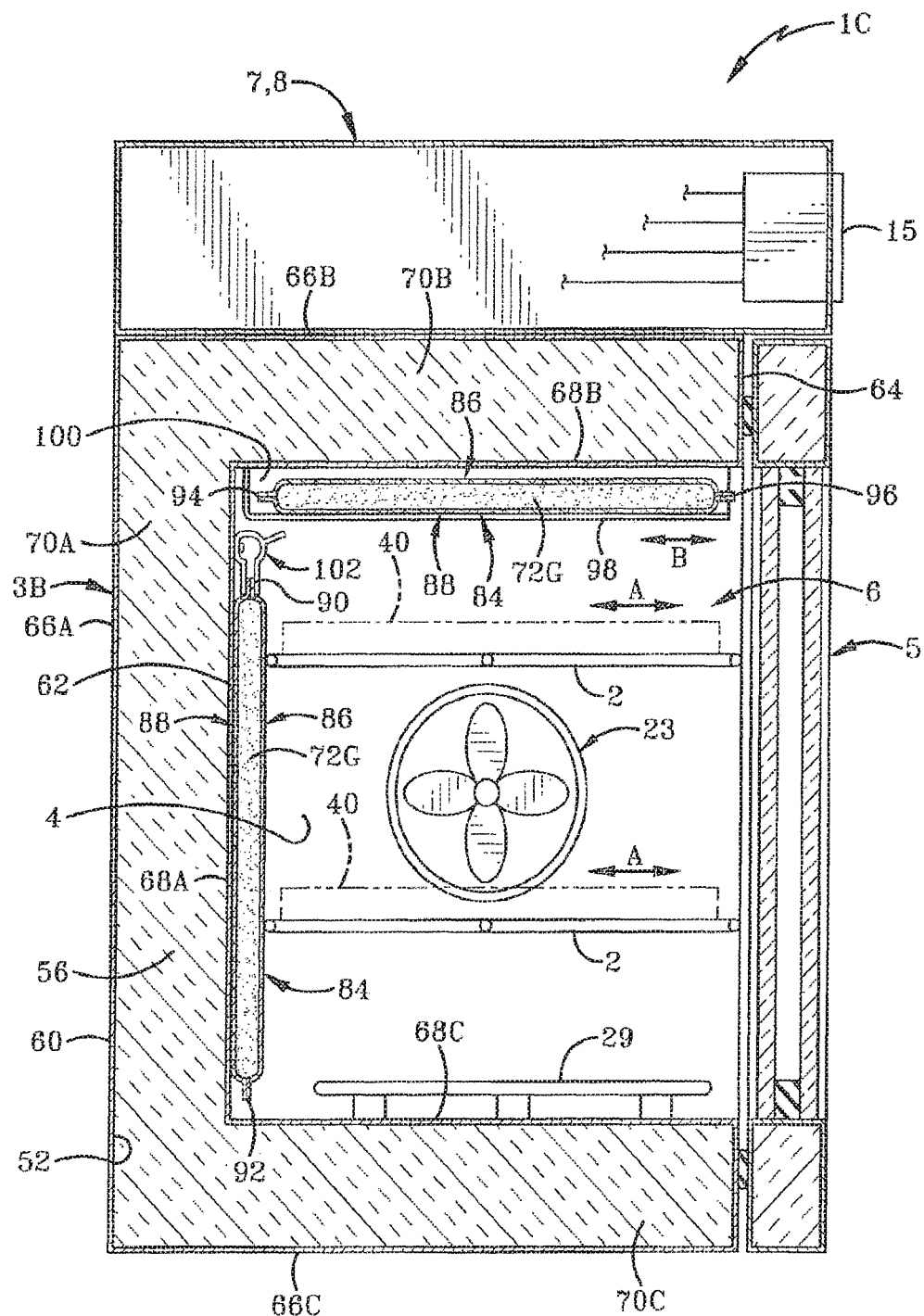
FIG. 8 is a sectional view similar to FIG. 7 of a fourth embodiment of the present invention also utilizing the phase change packets.
Figure 9:
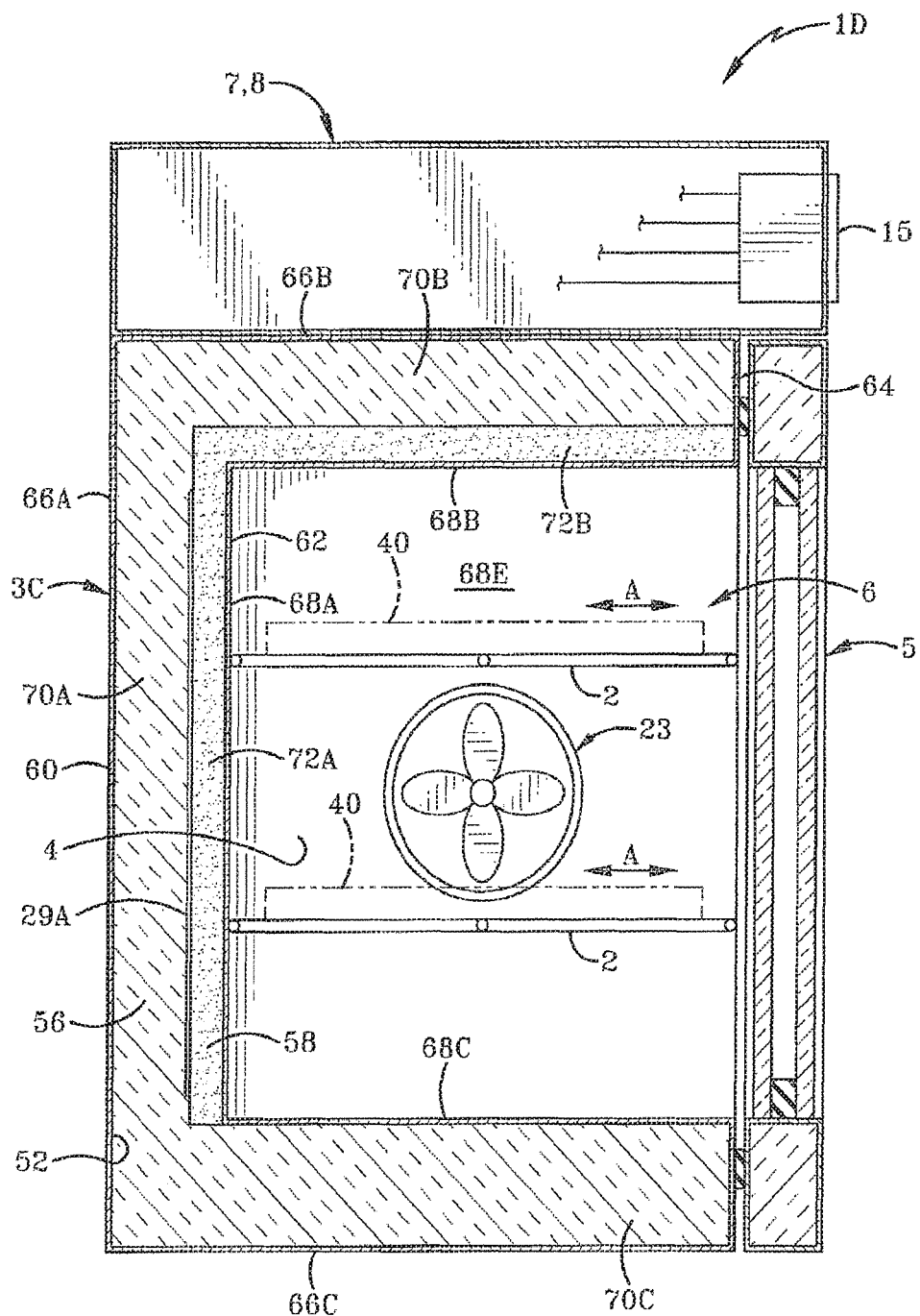
FIG. 9 is a sectional view similar to FIG. 2 of a fifth embodiment of the chamber of the present invention utilizing a heating element between the insulation and phase change material.
Figure 10:
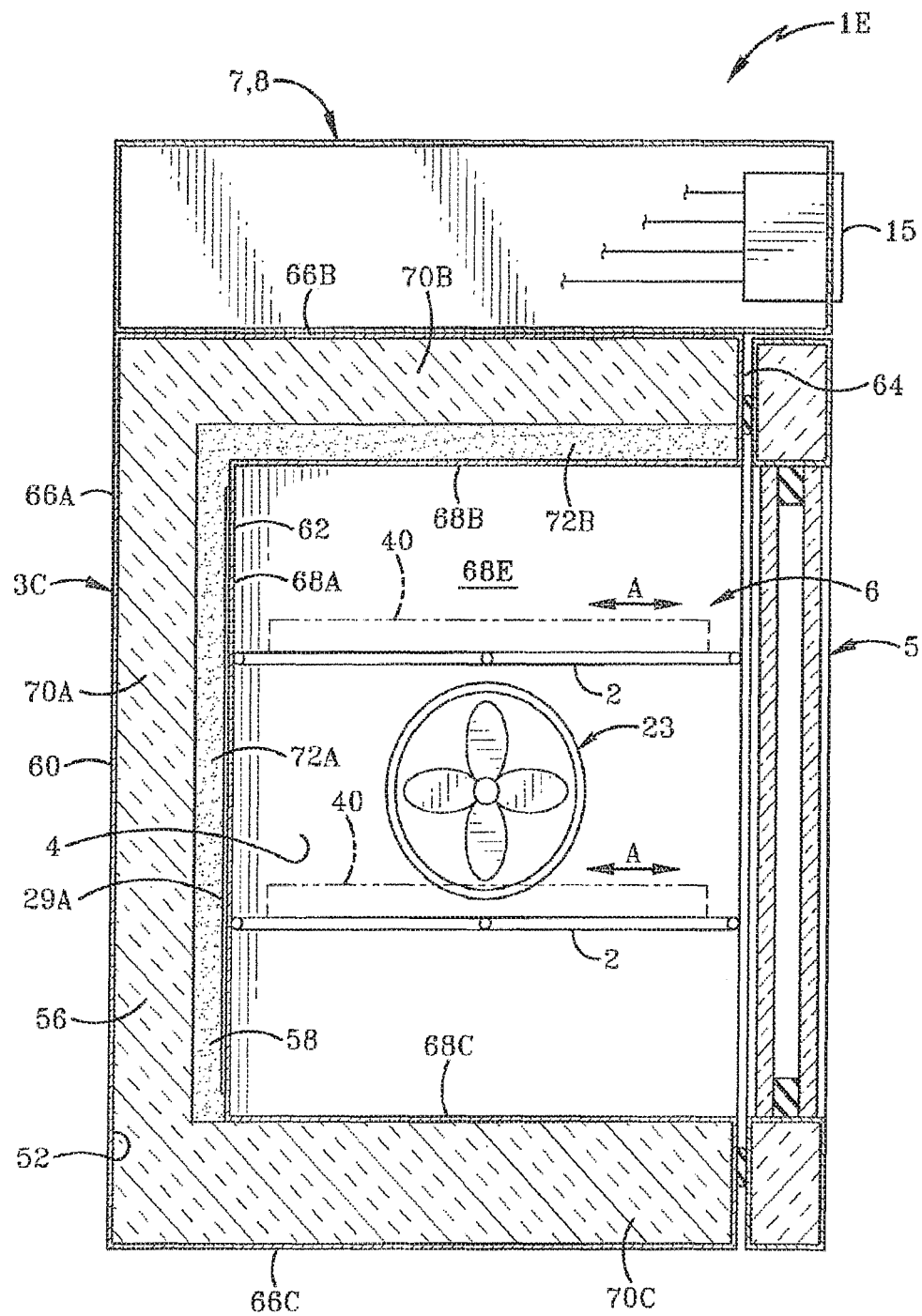
FIG. 10 is a sectional view similar to FIG. 9 of a sixth embodiment of the chamber of the present invention utilizing a heating element between the phase change material and the inner layer of the skin.
Figure 11:
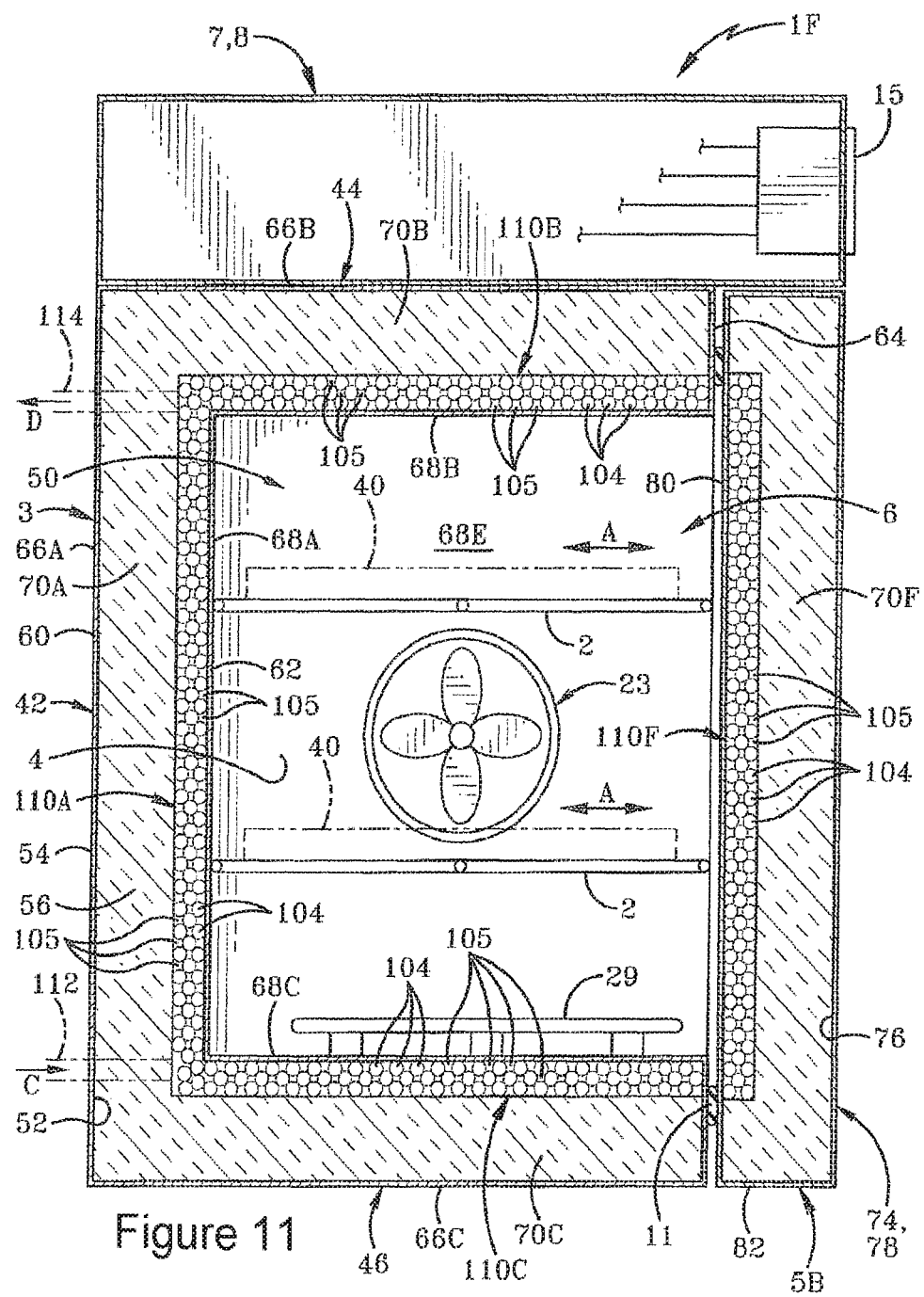
FIG. 11 is a sectional view similar to FIG. 5 of a seventh embodiment of the chamber of the present invention wherein the phase change material is contained within numerous encapsulated pellets which are within a liquid medium.
Figure 13:
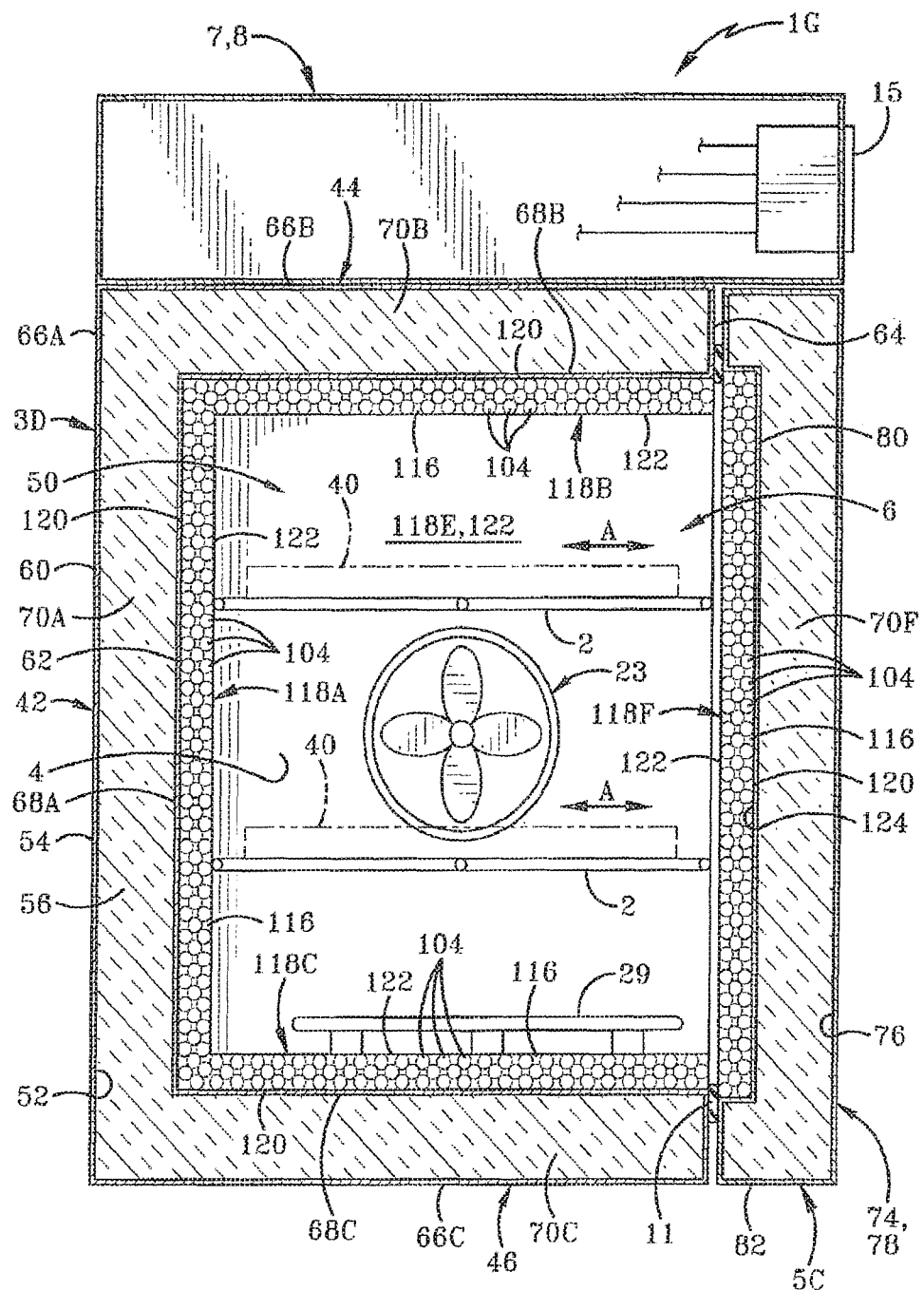
FIG. 13 is a sectional view similar to FIG. 12 of an eighth embodiment of the chamber of the present invention showing the phase change material within encapsulated pellets which are embedded in a solid matrix.
Figure 15:
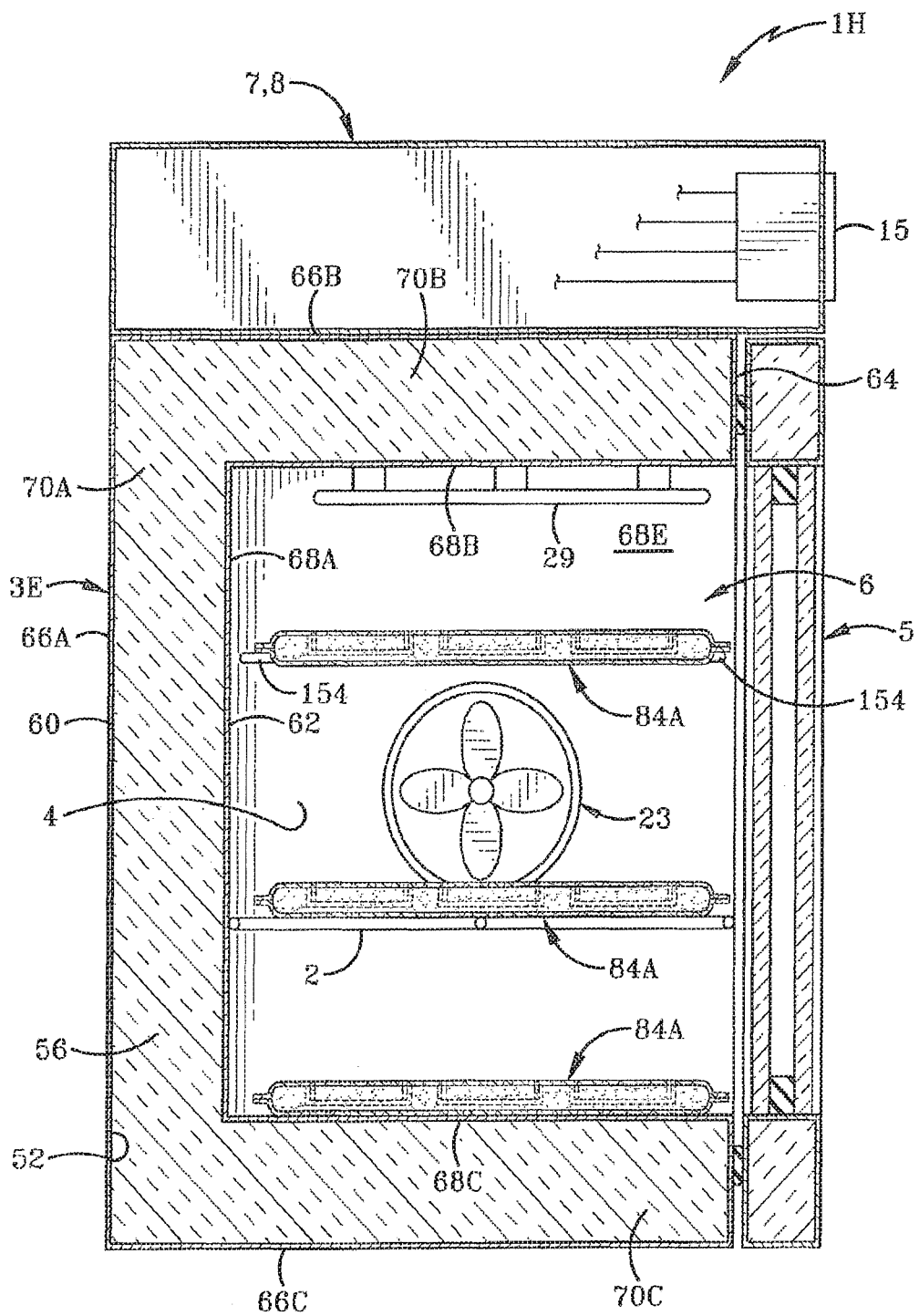
FIG. 15 is a sectional view similar to FIG. 7 of a ninth embodiment of the chamber of the present invention using the PCM packets or shelves shown in FIG. 14.

A first embodiment of the insulated enclosure or chamber of the present invention is shown generally at 1 in FIG. 1, with additional embodiments shown generally at 1A in FIG. 5, at 1B in FIG. 7, at 1C in FIG. 8, at 1D in FIG. 9, at 1E in FIG. 10, at 1F in FIG. 11, at 1G in FIG. 13, and at 1H in FIG. 15. Chamber 1 is configured to serve as an incubator, environmental chamber, oven, refrigerator or freezer. Chamber 1 includes a main body or container 3, a storage interior chamber 4 defined by container 3, a door 5 and a control assembly 7 secured to and seated atop container 3. Container 3 in the exemplary embodiment is in the form of a five-sided or five-walled box-like structure wherein the forward terminal ends of four of these walls define an entrance opening 6 (FIG. 2) of interior chamber 4. Upper and lower horizontal shelves 2 are disposed within interior chamber 4 extending between three of the walls of container 3 and suitably supported therein for supporting thereon one or more storage items 40 (dashed lines) to be stored in interior chamber 4 over a duration typically measured in hours, days, or weeks. Storage item 40 may, for example, be one or more petri dishes or other containers for growing cultures or for supporting other items which need incubation or heating in a controlled manner. Storage item 40 may also include the contents of a dish or container, such as a culture, and may include other components, some of which are discussed in greater detail further below. Item 40 may also be cooled in a controlled manner and frozen if desired. Insulated chamber is configured to heat and/or cool item 40 and/or to maintain item 40 within interior chamber 4 at a desired temperature, as described further below. Door 5 is hingedly attached to container 3 by hinges 9 to swing between open (FIG. 1) and closed (FIGS. 2, 4) positions. An annular sealing gasket 11 provides a seal between door 5 and container 3 when door 5 is closed, such that main body 3 and door 5 together form a six-sided or six-walled container or enclosure. Items 40 are removable from and insertable into (Arrows A in FIGS. 2, 5, 7-11 and 13) interior chamber 4 through entrance opening 6 when door 5 is open.

Door 5 includes a transparent window 12 which may be double paned (FIG. 2) with two parallel panes 16 (typically made of glass) with an annular elastomeric seal 18 therebetween and in contact therewith to separate panes 16 by a space 20. Space 20 is defined by the inner perimeter of seal 18 and panes 16 and is filled with gas or under vacuum to help thermally insulate interior chamber 4 when door 5 is closed to cover entrance opening 6. Door 5 includes a rectangular annular wall 10 which surrounds window 12 along its outer edges and is hollow and typically includes a metal skin which defines a rectangular annular insulated fully enclosed door interior chamber or compartment 13 with thermal insulation 14 therein which nearly or completely fills compartment 13.

Control assembly 7 includes an enclosure or housing 8 on which is mounted a manual control interface 15 and which houses a temperature control unit 17, a humidity control unit 19 and a carbon dioxide control unit 21. Interface 15 is in electrical communication with control units 17, 19 and 21, and also with a fan assembly 23 within or in communication with interior chamber 4 and an electric power source 25 outside housing 8. Temperature control unit 17 is in electrical communication with a temperature sensor 27 within or bounding interior chamber 4 and with an electric heating unit or device in the form of a heating coil 29 within interior chamber 4. Temperature control unit 17 is also in electrical communication with a cooling device or refrigeration assembly 28 which includes internal heat-exchanging pipes 30 and external components 32 which typically include external heat-exchanging pipes, a compressor, and an expansion valve such that the refrigeration assembly provides a typical refrigeration cycle whereby the refrigerant within the coils is capable of providing active cooling within interior chamber 4 via the internal coils 30 therein. Cooling and heating devices 28 and 29 serve as electrically powered temperature-altering devices for altering the temperature of interior chamber 4, items 40 and other components within chamber 4 and portions of the walls defining chamber 4. Humidity control unit 19 is in electrical communication with a humidity sensor 31 within or bounding interior chamber 4 and with an actuator such as a solenoid of a water control valve 33 which is in fluid communication with a water source 35. Thus, humidity control unit 19 is operatively connected to interior chamber 4 to control the amount of humidity within chamber 4. Carbon dioxide control unit 21 is in electrical communication with a carbon dioxide sensor 37 and an actuator such as a solenoid of a carbon dioxide control valve 39 which is in fluid communication with a carbon dioxide source 41. Thus, carbon dioxide control unit 21 is operatively connected to interior chamber 4 to control the level of carbon dioxide within chamber 4.

Main body or container 3 is now described in greater detail. Container 3 has several generally rigid walls or sidewalls including a flat vertical rectangular back wall 42, flat rectangular horizontal top and bottom walls 44 and 46 secured respectively to the top and bottom of back wall 42 and extending forward therefrom, and flat vertical left and right side walls 48 and 50 secured respectively to the left and right sides of back wall 42 and extending forward therefrom. Left and right side walls 48 and 50 are also secured to and extend between the respective left and right ends of top and bottom walls 44 and 46. Walls 42-50 thus form a box or cup-shaped configuration defining interior chamber 4 such that walls 44-50 at their front ends define entrance opening 6. A fully enclosed sealed rectangular cup-shaped interior cavity or chamber 52 is formed within container 3 separate from interior chamber 4 and more particularly is defined by a substantially rigid skin 54 which is typically formed of metal although it may be formed of a plastic or other suitable material. Chamber 52 surrounds interior chamber 4 on five sides thereof. Wall or sidewall chamber 52 is sealed from external atmosphere and is nearly or completely filled by insulation 56 and a phase change material 58 (PCM), each of which is also in a substantially rectangular cup-shaped configuration corresponding to that of chamber 52. The phase change material 58 is disposed between the insulation and interior chamber 4 along the entire inner surface of insulation 56 and thus essentially completely surrounds interior chamber 4 on all five sides of container 3. Thus, each of walls 42-50 includes several layers or materials. Insulation 56 may be formed of a variety of insulation materials which remain in a solid state throughout the operation of the chamber and which are generally rigid or compressible. For example, insulation 56 may be fiberglass, styrofoam, or various types of foam boards or sheets, such as those formed from polystyrene, polyurethane, polyisocyanurate and the like. Some of these insulation boards are referred to commonly as polyiso boards. PCM 58 is discussed in greater detail further below. Although PCM 58 is shown on all five sides of container 3 entirely surrounding interior chamber 4, chamber 1 may also be formed with PCM 58 on only one, two, three or four sides of container 3 so that PCM 58 is adjacent chamber 4, but does not surround chamber 4.

Skin 54 includes a rectangular cup-shaped outer layer 60, a rectangular cup-shaped inner layer 62 and a rectangular annular front layer 64 which is substantially vertical and extends between the front of outer and inner layers 60 and 62. Outer layer 60 thus forms outer layers of each of the walls of container 3, namely vertical rear outer layer 66A of back wall 42, horizontal top outer layer 66B of top wall 44, horizontal bottom outer layer 66C of bottom wall 46, vertical left outer layer 66D of left side wall 48 and vertical right outer layer 66E of right side wall 50. Inner layer 62 similarly forms the inner layers of each of these walls, namely vertical front inner layer 68A of back wall 42, horizontal bottom inner layer 68B of top wall 44, horizontal top inner layer 68C of bottom wall 46, vertical right inner layer 68D of left side wall 48 and vertical left inner layer 68E of right side wall 50. Each of layers 66 and 68 is flat and rectangular.

Insulation 56 likewise makes up insulation layers of each of the five walls of container 3 which abut the respective outer layer 66 thereof and extend inwardly therefrom part of the way toward the respective inner layer 68 thereof. More particularly, insulation 56 includes a vertical flat rectangular insulation layer 70A of back wall 42 which abuts the front inner surface of outer layer 66A and extends forward therefrom, a flat rectangular horizontal insulation layer 70B of top wall 44 which abuts the lower inner surface of outer layer 66D and extends downwardly therefrom, a flat rectangular horizontal insulation layer 70C of bottom wall 46 which abuts the top inner surface of outer layer 66C and extends upwardly therefrom, a flat rectangular vertical insulation layer 70D of left side wall 48 which abuts the inner surface of outer layer 66D and extends inwardly to the right therefrom, and a flat rectangular vertical insulation layer 70E of right side wall 50 which abuts the left inner surface of outer layer 66E and extends inwardly to the left therefrom.

PCM 58 also forms respective PCM layers of each of the walls of container 3, namely a vertical flat rectangular PCM layer 72A of back wall 42 which extends between and is in contact with the front inner surface of insulation layer 70A and the rear surface of skin inner layer 68A, a flat rectangular horizontal PCM layer 72B which extends between and is in contact with the bottom inner surface of insulation layer 70B and the top surface of inner layer 68B, a flat rectangular horizontal PCM layer 72C which extends between and is in contact with the upper surface of insulation layer 70C and the lower surface of inner layer 68C, a vertical flat rectangular PCM layer 72D which extends between and is in contact with the inner surface of insulation layer 70D and the left surface of inner layer 68D, and a flat rectangular vertical PCM layer 72E which extends between and is in contact with the left inner surface of insulation layer 70E and the right surface of inner layer 68E. Each PCM layer 17 is thus disposed within a cavity or portion of interior chamber 52 between the corresponding inner layer of the skin and layer of insulation 70.

Chamber 1A (FIG. 5) is similar to chamber 1 except that it includes a door 5A which is somewhat different than door 5 although both doors are substantially rigid and serve as a wall or sidewall of the chamber 1 or 1A. Unlike door 5, door 5A does not include a transparent window which allows someone to view the contents of interior chamber 4 from outside the chamber without opening the door. Instead, door 5A is opaque and has a configuration similar to one of the walls of container 3 and is thus made of several layers. In particular, door 5A includes a substantially rigid skin 74 which is relatively thin and typically formed of metal and defines a fully enclosed vertical rectangular interior cavity or chamber 76 which is separate from chambers 4 and 52, which is sealed from external atmosphere and in which are disposed an insulation layer 70F and a PCM layer 72F. Skin 74 includes outer end inner vertical rectangular layers 78 and 80 and a rectangular annular perimeter layer 82 which extends between and is secured to the respective outer perimeters of outer and inner layers 78 and 80 such that layers 78-82 define therewithin chamber 76. Insulation layer 70F extends from the top to the bottom and from the left side to the right side of interior chamber 76. Insulation layer 70F also abuts the inner surface of outer layer 78 and extends inwardly and rearwardly therefrom and may contact the front inner surface of inner layer 80 along its outer perimeter although insulation layer 70F only extends part of the way towards inner layer 80 along a rectangular portion of door 5A which is directly in front of entrance opening 6. PCM layer 72F is a flat vertical rectangular layer which extends between and abuts the front surface of inner layer 80 and the rear surface of insulation layer 70F such that when door 5A is closed, PCM layer 72F entirely covers or spans the entrance opening 6 of interior chamber 4. PCM layer 72F is thus disposed within a cavity or portion of the sidewall or door interior chamber 76 defined between inner layer 80 and insulation layer 70F. PCM layer 72F is intended to be permanently disposed within chamber 76 and is thus not removable therefrom, just as the PCM layers 72A-E are not removable from interior chamber 52 of container 3.

Figure 6:
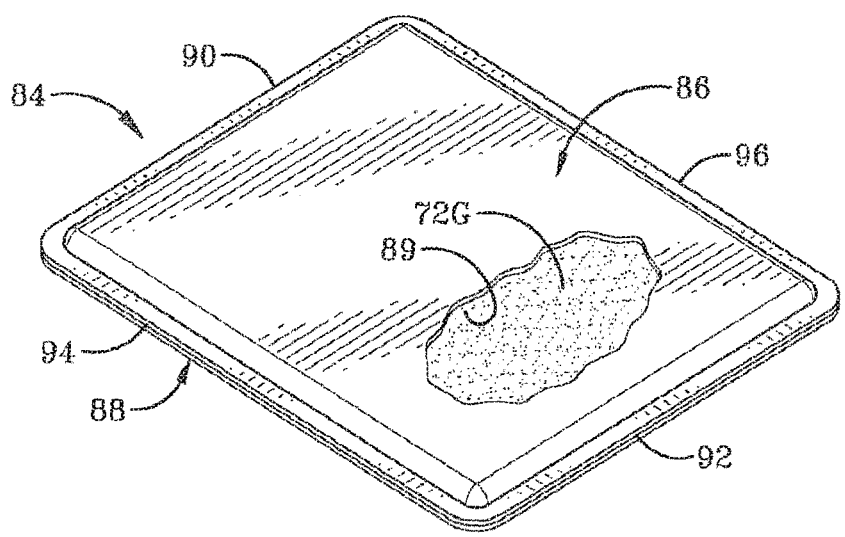
FIG. 6 is a perspective view with portions cut away of the removable and repositionable phase change material packet or wall of the present invention.

FIG. 6 illustrates a removable PCM packet 84 which is typically easily carried by one person and otherwise manipulated with one or two hands for use with chambers configured to receive packet 84. Packet 84 includes first and second substantially flat rectangular walls 86 and 88 which together form an outer skin and overlay one another such that their outer perimeters are superimposed and in contact with one another while the vast majority of walls 86 and 88 are spaced from one another to define therebetween a flat rectangular interior cavity or chamber 89 which receives therein a flat rectangular PCM layer 72G which nearly or completely fills chamber 89. Walls 86 and 88 are preferably formed of a substantially rigid thermally conductive material, such as a metal. Aluminum, stainless steel and copper are well suited for this purpose. However, walls 86 and 88 may be formed of a plastic or other suitable material. Packet 84 has first and second opposed straight parallel end edges 90 and 92, and first and second straight parallel opposed side edges 94 and 96 which extend respectively between end edges 90 and 92 so that edges 90-96 form a rectangular configuration along the outer perimeters of walls 86 and 88. Walls 86 and 88 are sealed to one another along each of edges 90-96 so that interior chamber 89 is fully enclosed and sealed from external atmosphere.

Chamber 1B is shown in FIG. 7 and utilizes removable PCM packets 84. Chamber 1B is similar to chambers 1 and 1A and is shown with door 5 although a door such as door 5A may also be used. Chamber 1B includes a container 3A which is similar to container 3 except that the insulation entirely or nearly entirely fills the interior chamber 52 since the PCM material is provided in packets 84 instead of within interior chamber 52. Thus, for example, the insulation layer 70A in the back wall of container 3A extends all the way from the front surface of outer layer 66A to the back surface of inner layer 68A. Similarly, insulation layer 70B extends continuously from the bottom surface of outer layer 66B to the top surface inner layer 68B, and insulation layer 70C extends all the way from the bottom surface of inner layer 68C to the top surface of outer layer 66C. The insulation layers in the two side walls of container 3A also extend all the way between the respective inner and outer layers thereof.

As shown in FIG. 7, the heating element 29 of chamber 1B is mounted on the top wall of container 3 within interior chamber 4 adjacent the top thereof. FIG. 7 further illustrates three of the removable PCM packets 84 within interior chamber 4. One of packets 84 is seated on top inner layer 68C of the bottom wall of container 3, which thus serves as a supporting structure or permanent shelf for the lower packet 84. Chamber 1B further includes a pair of horizontal trays 98 which respectively hang downwardly from the wire or other type shelves 2 such that each tray and the respective shelf are adjacent one another and define therebetween a respective rectangular flat horizontal packet-receiving space 100 for removably inserting therein a respective packet 84 through a front entrance opening of a respective space 100. Thus, the lowermost packet 84 is directly below the other two packets as well as directly below the two shelves and trays, and spaced downwardly from the lower tray. The middle packet 84 is thus seated atop the lower tray 98 below and adjacent the lower removable shelf 2. Similarly, the top or upper packet 84 is seated atop the upper tray 98 below and adjacent the removable upper shelf 2. In addition, the upper tray 98 is spaced upwardly from the lower shelf 2 so that a portion of interior chamber 4 is defined between the top of the lower shelf 2 and the bottom of tray 98 inasmuch as the upper tray 98 and the corresponding upper packet 84 is spaced upwardly from the lower shelf 2. This portion of interior chamber 4 receives petri dishes or other items 40 which are seated on the lower shelf 2 so that the temperature of item 40 and the environment in interior chamber 4 surrounding item 40 may be controlled. Items 40 are thus adjacent, above and out of contact with the respective packet 84 during the process of temperature and other environmental control in interior chamber 4. Similarly, interior chamber 4 includes an upper portion above the upper shelf 2 also configured to receive items 40, which are likewise adjacent, above and out of contact with the upper packet 84 during the process of thermal and other environmental control within interior chamber 4. As previously noted, each packet 84 may be inserted and removed from its respective space 100 or from atop the bottom wall (Arrows B in FIGS. 7, 8) through the entrance opening 6 when door 5 is open. Trays 98 serve as PCM packet shelves. However, PCM packets 84 may also be seated on shelves 2 or another support so that items 40 may be seated directly on packets 84.

Chamber 1C (FIG. 8) is similar to the previous chambers and includes a container 3B which is similar to but somewhat modified from the earlier containers. The insulation within interior chamber 52 of container 3B is the same as that described with reference to the insulation within container 3A of chamber 1B. As shown in FIG. 8, the heating element 29 is mounted adjacent and above the bottom wall of the container within interior chamber 4 in the same manner as with chamber 1. Chamber 1C illustrates the use of two PCM packets 84 in a different orientation than that shown with chamber 1B. A tray 98 is mounted on the top wall of container 3B within the upper portion of interior chamber 4 so that the upper PCM packet may slide horizontally (Arrow B in FIG. 8) to be inserted or removed from the space 100 above tray 98 and below and adjacent the top wall of container 3B. The other packet 84 is positioned in a vertical orientation behind removable shelves 2 abutting or adjacent the front inner surface of inner layer 68A of the back wall of container 3B. More particularly, a clip 102 is secured to the back wall adjacent the top wall of the container and clips or clamps the first end edge 90, which serves as the top of packet 84 in the vertical orientation in order to suspend packet 84 in this rearward position. As will be appreciated, any suitable mechanism may be used in order to secure packet 84 in its hanging position or a vertical position closely adjacent the back insulating wall. PCM packets 84 of insulated chamber 1B and 1C are positioned so that they do not hinder the insertion and removal of items 40 from interior chamber 4, that is, items 40 may be inserted and removed without moving PCM packets from their respective positions within chamber 4. In addition, packets 84 are configured so that PCM 72G (like the non-removable PCM 56 of chamber 1) is not visible to the end user of the insulated chambers 1B and 1C. Moreover, PCM packets 84 are configured and positioned in chamber 4 so that the space normally reserved for items 40 on shelves 2 (i.e., without the use of packets 84 or trays 98) is not substantially reduced, and in most cases the reduction in available space for items 40 is not significant enough to have any real impact. Thus, the items 40 normally placed in a chamber 4 of a given size may still be placed therein with the addition of trays 98 and/or packet(s) 84. Although not shown, it is contemplated that a packet 84 may be positioned in a space behind or adjacent a "false" wall within chamber 4 such that the packet is hidden and whereby heat transfer to and from the packet is largely by convection. For example, such a false wall may be situated in front of the vertical packet 84 shown in FIG. 8.

Figure 2:
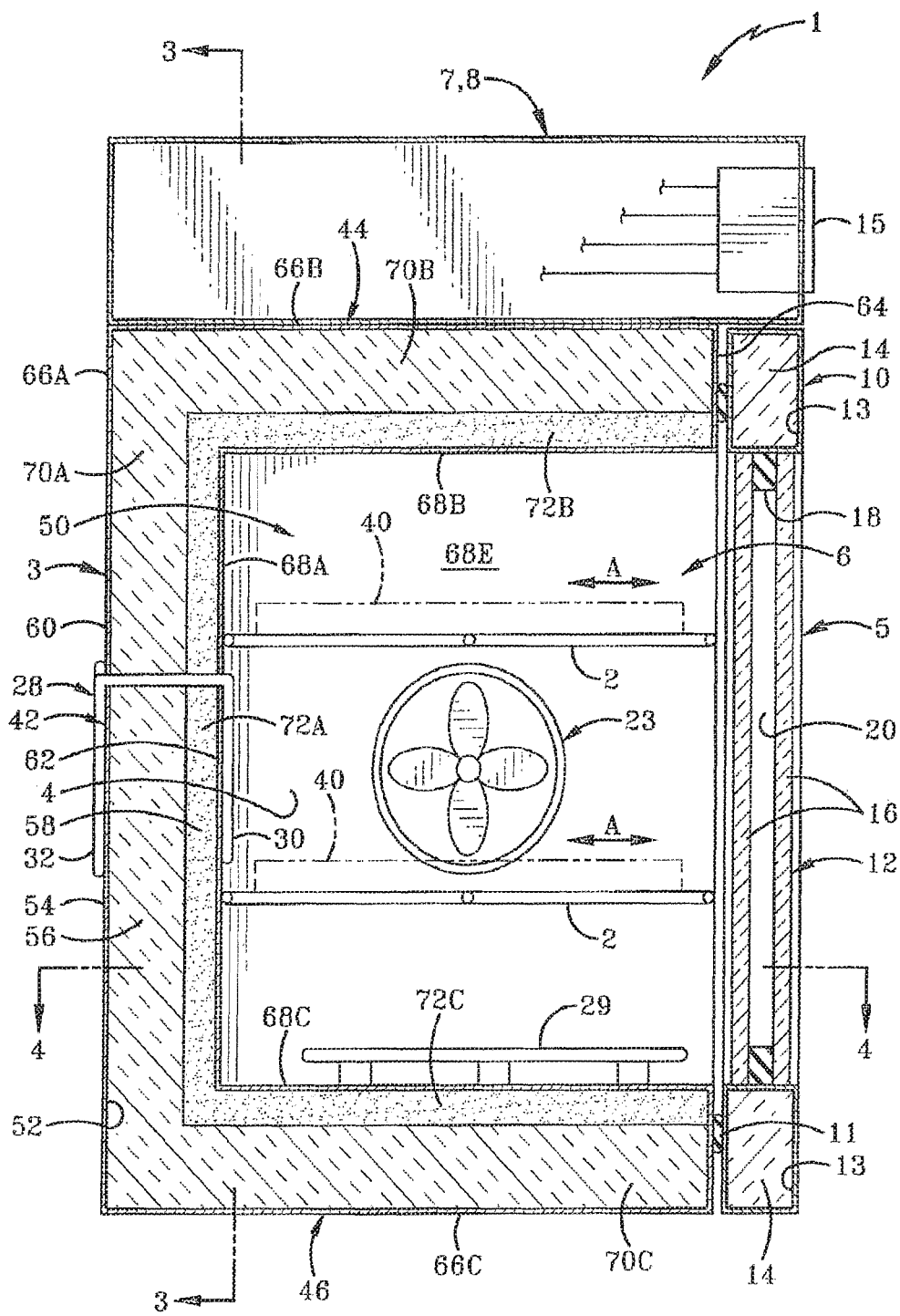
FIG. 2 is a sectional view taken on Line 2-2 of FIG. 1.
Figure 3:
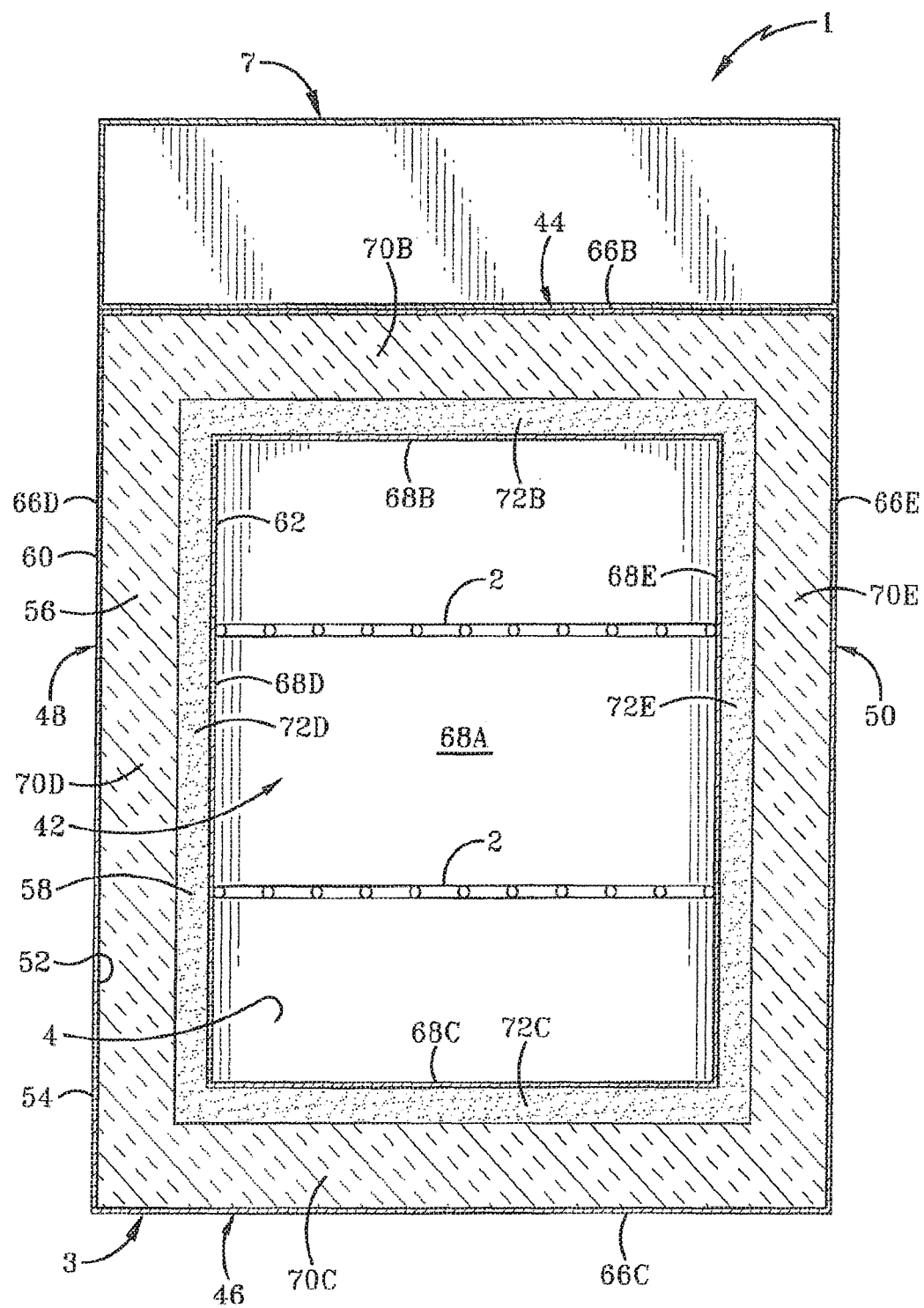
FIG. 3 is a sectional view taken on Line 3-3 of FIG. 2.

Chamber 1D (FIG. 9) is similar to the previous chambers and includes a modified container 3C such that the interior chamber 52 contains insulation, PCM, and a heating element 29A sandwiched therebetween. The insulation layer 70C of chamber 1D is substantially the same as that described with regard to the chambers 1B and 1C in FIGS. 7 and 8. Similarly, the insulation in the left and right side walls of container 3C completely or nearly fills the portions of chamber 52 within the respective left and right side walls of container 3C. The insulation layers 70A and 70B of container 3C are substantially the same as those of chamber 1, as illustrated in FIGS. 2 and 3. In addition, the PCM layers 72A and 72B within container 3C are substantially the same as that shown and described with reference to FIGS. 2 and 3 of chamber 1. In chamber 1D, only these two PCM layers 72A and 72B are used such that the bottom wall and left and right side walls of container 1D do not include such PCM layers. As FIG. 9 illustrates, interior chamber 4 is free of a heating element such as heating element 29 of the previous embodiments. Instead, heating element 29A is sandwiched between insulation layer 70A and PCM layer 72A and is thus substantially vertically oriented and in contact with each of said layers. Element 29A is thus entirely external to interior chamber 4.

Chamber 1E (FIG. 10) is similar to chamber 1D except that it includes a heating element 29A which is sandwiched between PCM layer 72A and inner layer 68A. Element 29A is thus in contact with the rear surface of layer 68A and the front surface of PCM layer 72A.

Figure 12:
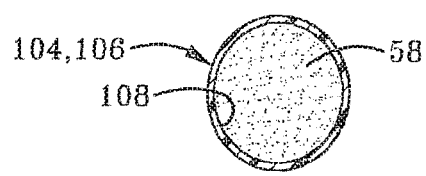
FIG. 12 is a sectional view of one of the encapsulated pellets.

Chamber 1F (FIG. 11) is similar to chamber 1A (FIG. 5) except that the various layers 72 of PCM 58 are replaced by numerous encapsulated PCM pellets 104 and a liquid medium 105 in which the pellets 104 are disposed. As shown in FIG. 12, each pellet 104 includes a solid capsule 106 having an inner surface which defines an interior chamber 108 or an enclosure which is sealed from the external atmosphere or environment by the solid skin or capsule 106. Interior chamber 108 is nearly or completely filled with PCM 58. As shown in FIG. 11, the mixture of pellets 104 and medium 105 form layers 110 which include a substantial amount of PCM 58 and are analogous to layers 72. While layers 110 may be on all sides of interior chamber 4, FIG. 11 shows only layers 110A, 110B, 110C and 110F, which are respectively analogous to layers 72A, 72B, 72C and 72F. Typically, pellets 104 are packed in as tightly or nearly as tightly as they can within the portion of interior chamber 52 defined between insulation 56 and inner layer 62 of skin 54. Pellets 104 are similarly packed into the portion of interior chamber 76 of the door between the insulation layer 70F and inner layer 80 of skin 74. Pellets 104 define therebetween interstitial spaces which are typically completely or nearly filled by liquid medium 105. Although in the exemplary embodiment, medium 105 is in a liquid form, it may also be in a gaseous form. In any case, the interior chamber 52 is completely or nearly filled by insulation 56, pellets 104 and medium 105. Similarly, the interior chamber 76 of the door is nearly or completely filled with insulation 70F, pellets 104 and medium 105.

As shown in dashed lines in FIG. 11, chamber 1F may include an inlet 112 and an outlet 114 communicating with the portion of interior chamber defined between insulation 56 and inner layer 62 of skin 54 such that a liquid or a mixture of pellets 104 and liquid medium 105 may be pumped or otherwise moved into this portion of the interior cavity via inlet 112 (arrow C) and out of this portion of the interior cavity through outlet 114 (arrow D). The provision of an inlet and an outlet is one manner of filling this portion of the interior chamber 52 with pellets 104 and medium 105, and also would allow for the pellets and medium to be removed via outlet 114 and, if desired, replaced with another set of pellets and liquid medium in which the PCM 58 of the pellets has a different melting or freezing temperature than that of the original pellets. It is noted that liquid 105 may be a phase change material which serves in the same fashion as PCM 58, or it may remain in a liquid state within the operational parameters of chamber 1F. The illustration with the use of inlet 112 and outlet 114 may represent the type of insulated chamber which uses a water jacket. Thus, instead of using the water jacketed insulated chamber in the standard manner, pellets 104 and liquid medium 105 may instead be used to fill the interior chamber of the water jacket in order to utilize the advantage of PCM 58 of the present invention.

Chamber 1G (FIG. 13) is similar to chamber 1F in that it also utilizes PCM pellets 104. However, instead of pellets 104 being disposed within liquid medium 105, pellets 104 of chamber 1G are embedded in a solid matrix 116. More particularly, the matrix 116 and embedded pellets 104 form respective flat rectangular layers 118 which are analogous to PCM layers 72A-F and layers 110 such that each of the layers is flat and rectangular and either horizontal or vertical as previously discussed with respect to layers 72. FIG. 13 shows specifically layers 118A-C, 118E and 118F. However, unlike layers 72 and layers 110, layers 118 are in the exemplary embodiment not within the interior chamber 52 defined by skin 54 of such chambers as chamber 1, 1A and 1F. Although layers 118 could be positioned within chamber 52 in the analogous positions of layers 72 and 110, the use of layers 118 illustrates one manner of forming layers comprising PCM 58 wherein the layers are external to interior chambers 52 and 76. Thus, chamber 1G may include a container 3D and a door 5C each of which has a somewhat different configuration than those of the previous embodiments. Container 3D retains skin 54 and its various layers to define there within the interior chamber 52. However, insulation 56 itself either completely or nearly fills interior chamber 52. FIG. 13 shows that inner layers 68 of skin 54 are positioned closer to the corresponding outer layers 68 such that outer layers 66 abut the outer surface of insulation 56 and the inner layer 68 abut the inner surface of insulation 56. Thus, insulation 56 in FIG. 13 appears to have the same thickness as insulation 56 in FIG. 11. However, the inner and outer layers 66 and 68 may also be spaced apart from one another as in the previous embodiments such that insulation 56 still fills the entire chamber 52 and is thicker, as shown in FIG. 7.

Each of layers 118 has an outer surface 120 and an inner surface 122. Each outer surface 120 of a given layer 118 which is part of container 3D abuts an inner surface of a corresponding inner layer 68 so that each layer 118 extends inwardly therefrom to inner surface 122. Thus, for instance, outer surface 120 of layer 118A is vertical and abuts the vertical inner surface of back inner layer 68A and extends inwardly therefrom to vertical surface 122 of layer 118A. The outer surface 120 of layer 118B serves as a top surface which thus abuts the inner or bottom surface of top inner layer 68B so that layer 118B extends downwardly therefrom to the horizontal inner or bottom surface 122 thereof. The outer surface 120 of layer 118C thus serves as a bottom horizontal surface from which layer 118C extends upwardly to the inner or top horizontal surface 122 thereof. The left and right walls of container 3D are formed in a similar manner to the back wall thereof such that the corresponding layer 118 is vertical, and the inner and outer surfaces 120 and 122 of the corresponding vertical layers 118 (layer 118E shown in FIG. 13) are vertical and oriented such that the outer layer 120 abuts the corresponding inner layer 68 and extends inwardly therefrom to the vertical inner surface 122. Thus, the inner surfaces 122 of the layers 118 define interior chamber 4, unlike the earlier embodiments in which the inner layers 68 of skin 54 defined interior chamber 4.

Although door 5C is similar to the doors of the earlier embodiments, it also differs somewhat in that inner layer 80 defines a vertical flat rectangular recess 124 in which layer 118F is received with its vertical outer or front surface 120 abutting the vertical inner surface of layer 80 and extending forward therefrom to the flat vertical inner or rear surface 122, which bounds interior chamber 4 when door 5C is closed. Although layer 118F is shown disposed in recess 124, a layer similar to 118F may be mounted on a door without such a recess and thus project forward beyond the forward most portion of the inner skin.

In the exemplary embodiment, solid matrix 116 is typically formed of a cured resin. Thus, during formation of layers 118, the original material which ultimately becomes matrix 116 is a liquid resin or in liquid form and thus cures to form the solid resin. In one embodiment, pellets 104 are mixed into a paint, which can then be painted onto any given surface, such as the inner layer 62 and the inner layer 80 and then allowed to dry. Paints typically contain a resin and a solvent, such that when the solvent dries, the resin is allowed to cure by chemical reaction. Some paints are also thermosetting, meaning that they are also heated in order to cure the resin. In another embodiment of solid matrix 116, the resin may not include a solvent which needs to dry in order to cure. For example, some resins are simply heat cured from a liquid state to a solid state without or with extremely minimal evaporation of components making up the liquid resin. Other liquid resins may be light cured in order to reach the solid state.

Thus, the layers 118 may be formed in several different ways. Where the matrix and its liquid form is a paint, the paint with pellets 104 mixed into it may simply be painted onto a given desired surface and allowed to dry. Another option is to pour a given liquid resin with the pellets 104 mixed therein into a cavity or recess such as recess 124 (such as when door 5C is laid horizontal with the recess 124 facing upwardly), and either allowed to dry, as with the paint, or cured by heat, light or any other suitable method in order to cure the resin within the recess. Alternately, any of the layers 118 may be independently formed in a mold cavity and subsequently mounted in the positions shown in FIG. 13 by any suitable mechanism. For instance, the bottom layer 118C may simply be laid atop the inner layer 68C, or may be adhered with a glue or another adhesive thereto. The other layers 118 may similarly be adhered by a glue or an adhesive or so forth. Further, the various layers 118 of container 3D may be formed as a single cup-shaped piece. Such formations may be done in a separate mold, or may use the inner layer 62 of skin 54 to define a portion of the mold. Matrix 116 may have varying degrees of thermal conductivity. The thermal conductivity may be enhanced by incorporating metal chips or other materials which are highly thermally conductive into the liquid resin during formation of the layers 118.

Figure 14:
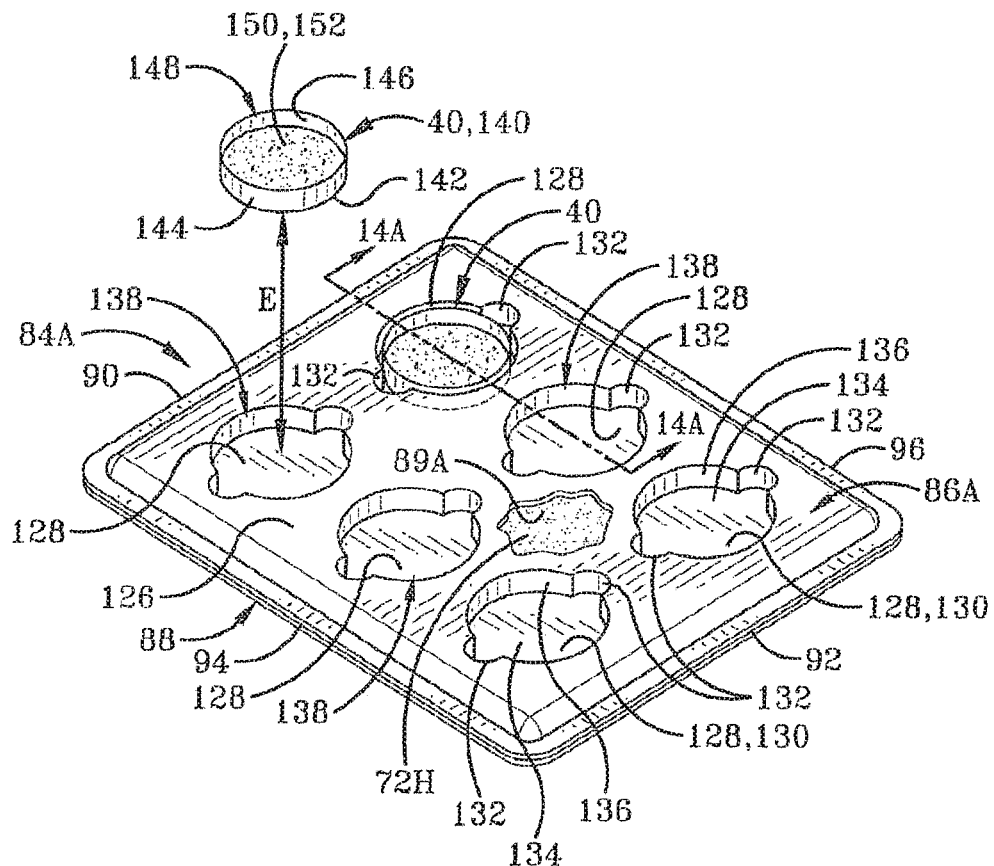
FIG. 14 is a perspective view of a PCM packet or shelf having recesses formed therein for receiving respective storage items.

FIG. 14 shows another PCM packet or shelf 84A which is similar to packet 84 shown in FIG. 6. Shelf 84A thus includes generally flat rectangular bottom wall 88 and a generally flat rectangular top wall 86A which define therebetween an interior chamber 89A which is filled with a layer 72H of PCM. PCM layer 72H typically completely or nearly fills interior chamber 89A. It is noted that PCM layer 72H of packet 84A or PCM layer 72G of packet 84 (FIG. 6) may be replaced with pellets 104, along with a gas or liquid medium 105 (FIG. 11) or embedded in solid matrix 116 (FIG. 13). Walls 86A and 88 are formed of the same materials as previously described with regard to packet 84, and are joined to one another to form end edges 90 and 92, and side edges 94 and 96. Unlike wall 86 of packet 84, which is substantially flat in a continuous manner from adjacent edge 90 to adjacent edge 92 and from adjacent edge 94 to adjacent edge 96, wall 86A includes an upper flat portion 126 which extends from adjacent edge 90 to adjacent edge 92 and from adjacent edge 94 to adjacent edge 96, but is interrupted by a plurality of recesses 128 extending downwardly therefrom. In the exemplary embodiment, packet 84A includes six recesses 128 although the number may vary depending on the size of the packet and the specific need. Although recesses 128 may be of any desired shape, each recess 128 is shown with a circular central portion 130 and a pair of opposed finger receiving portions 132 which extend laterally outwardly from central portion 130 on opposite sides thereof and away from one another. The bottom of each recess 128 is defined by a flat horizontal recessed wall 134 which is spaced downwardly from upper flat portion 126. An annular side wall 136 at its lower end is rigidly secured to and extends upwardly from the outer perimeter of recessed wall 134 to a rigid connection at its upper end to upper flat portion 126, whereby each recessed wall 134 and the corresponding side wall 136 defines the corresponding recess 128. Each recess 128 has a top entrance opening 138 through which a given storage item 40 may be downwardly inserted and upwardly removed, as indicated at arrow E in FIG. 14.

With continued reference to FIG. 14, the specific storage item 40 includes a container or petri dish 140 having a flat circular bottom wall 142 and a circular annular side wall 144 rigidly secured to and extending upwardly from the bottom wall 142 to define there within a cylindrical cavity 146 with a top entrance opening 148. Cavity 146 is thus configured to receive various contents via entrance opening 148 and/or have the contents removed thereby. In the exemplary embodiment, item 40 includes the contents, which are in the form of a culturing medium 150 with living cells 152 to be grown or cultured thereon.

Figure 14A:
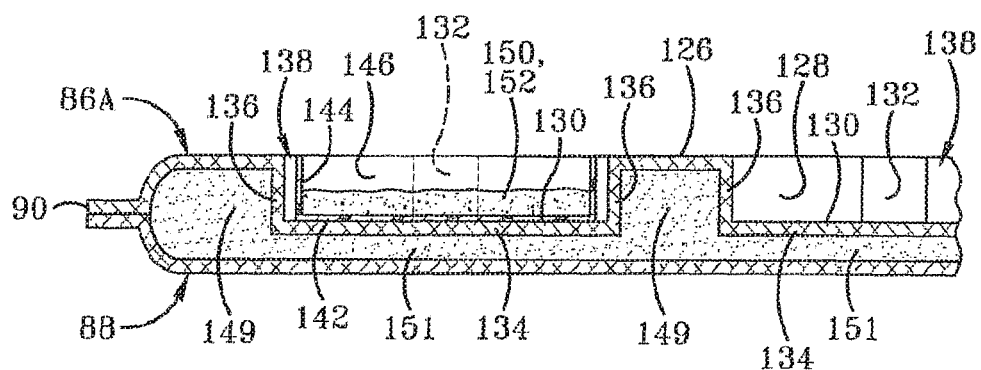
FIG. 14A is a sectional view taken on line 14A-14A of FIG. 14.

The sectional view of FIG. 14A illustrates the relative positions of the petri dish 140 and its contents to the corresponding recess 128 and various components of the packet 84A, including the PCM. The PCM of layer 72H includes a lateral portion or portions 149 which may also be referred to as a recess-surrounding portion. The PCM of layer 72H also includes respective sub-recess portions 151 which are located directly below the corresponding recess 128 and recessed wall 134. The lateral portions 149 extend laterally outwardly from annular side wall 136 in all directions so that this portion of the PCM, as viewed from above, surrounds the corresponding annular side wall 136, as well as the bottom wall 134, recess 128, and when petri dish 140 is disposed within 128, also the bottom wall 142 thereof, at least a portion of side wall 144, and all or part of medium 150 and cells 152. Portions 149 have a top surface which abuts the bottom surface of upper flat portion 126 whereby the PCM of layer 72H extends from below recessed wall 134 and the bottom of petri dish 140 to above recessed wall 134, bottom wall 142, most or all of side wall 144 and all or part of medium 150 and cells 152. In the exemplary embodiment, bottom wall 142 of dish 140 is seated on horizontal flat recessed wall 134 with annular side wall 144 abutting or closely adjacent annular side wall 136, which typically has a substantially similar shape as side wall 144 as viewed from above so that the petri dish side wall and the contents of the dish are adjacent portions 149 of PCM. In the exemplary embodiment, the top of the petri dish is no higher than the top of the top of upper flat portion 126 although this may vary. Likewise, the medium 150 and cells 152 are typically no higher than the top of portion 126.

Referring now to FIG. 15, chamber 1H is configured to use the packets or shelves 84A shown in FIG. 14. Chamber 1H is similar to chamber 1B shown in FIG. 7 except that chamber 1H shows a different shelving configuration. FIG. 15 illustrates that the lower packet or shelf 84A is removably positioned atop inner layer 68C of the bottom wall, similar to the lower packet 84 in FIG. 7. However, the middle packet or shelf 84A is seated atop a wire or other shelf 2 rather than on a tray 98 as in FIG. 7. The bottom walls 88 of each of the lower and middle shelves or packets 84A are atop a supporting surface or shelf whereby each packet 84A serves as a shelf on which the various items 40 are seated within interior chamber 4. The upper shelf 84A of chamber 1H is supported within interior chamber 4 in a different manner. More particularly, support ledges 154 are connected to and extend inwardly from the left and right walls defining interior chamber 4 in order to support the upper packet 84A respectively along its left and right side edges 94 and 96. FIG. 15 shows only one of support ledges 154, which extends from adjacent the back of interior chamber 4 to adjacent the front of interior chamber 4. Thus, packet 84A along the left and right edges 94 and 96 form respective lips which are seated on the support ledges 154. These lips or side edges of packet 84 easily slide along support ledges 154 to insert the packet or shelf 84A into chamber 4 or remove it therefrom via entrance opening 6 when door 5 is opened.

Figure 17:
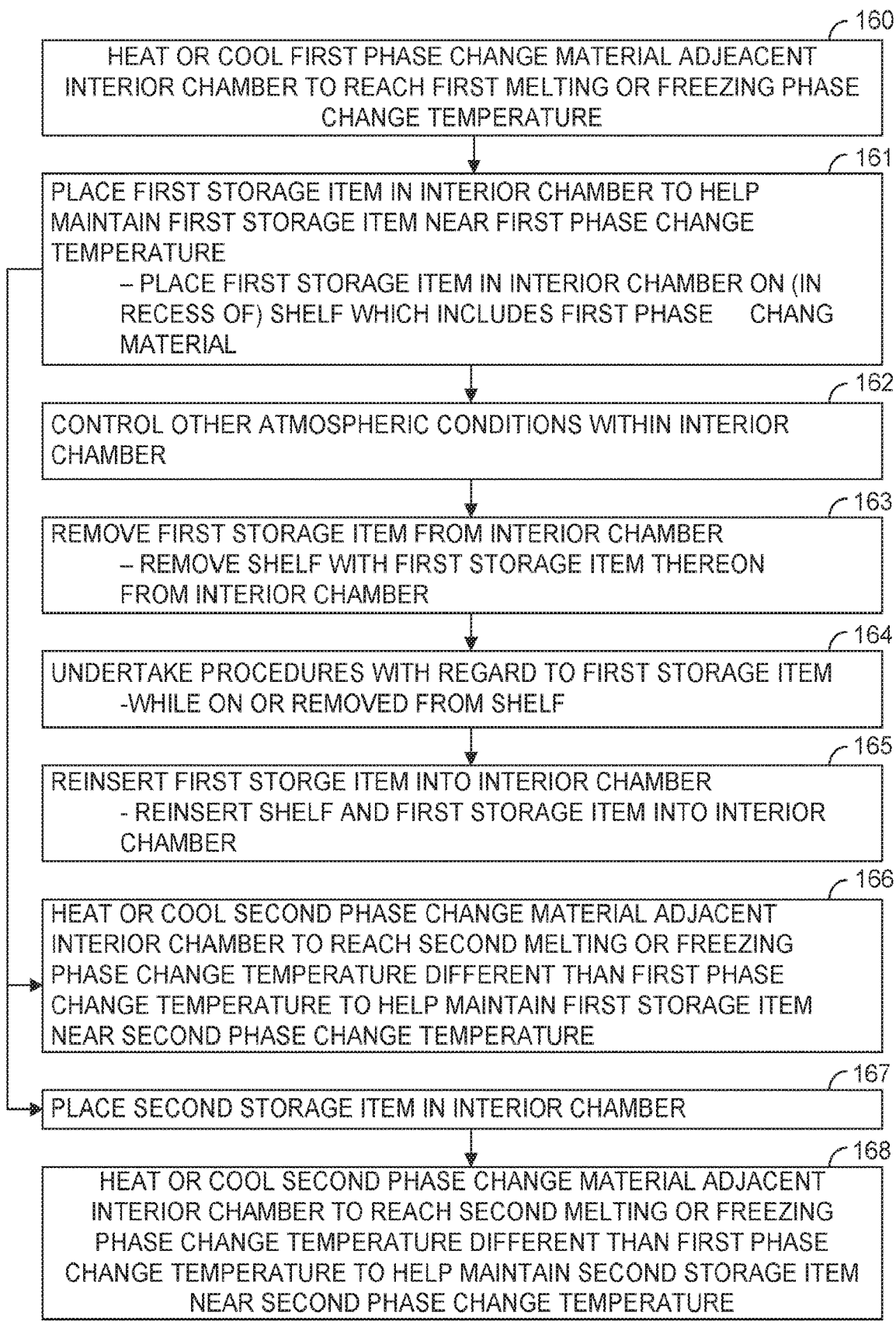
FIG. 17 is a flow chart illustrating various methods of the present invention.

Although each of the chambers described above vary somewhat from one another, all of them operate in essentially the same basic manner. Various processes of the present invention are illustrated in the flow chart of FIG. 17 at blocks 160-168 and will be referred to hereafter although not necessarily in the same order. Each insulated chamber is configured to control various atmospheric conditions within interior chamber 4 (block 162). For example, power source 25 provides the power for running the various electrical components of chamber 1, such as fan assembly 23, control units 17, 19, and 21, refrigeration assembly 28, heating unit 29 and the solenoid or other actuator of control valves 33 and 39. The user of chamber 1 manipulates the settings of temperature, humidity and $CO_2$ level within interior chamber 4 via control interface 15, which may include three or more buttons or controls as shown in FIG. 1 which correspond respectively to these three features. Sensors 27, 31 and 37 respectively sense or determine the temperature, humidity and $CO_2$ level within interior chamber 4 and produce respective signals which are sent respectively to temperature control unit 17, humidity control unit 19 and $CO_2$ control unit 21. Based on the signal from temperature sensor 27, temperature control unit 17 controls heating unit 29 to turn it off, turn it on and/or control the degree of heat produced thereby for providing heat within interior chamber 4 as well as heat to PCM material 58 radiated through the various inner layers 68 of skin 54. Temperature control unit 17 may also control refrigeration assembly 28 in response to the signal from temperature sensor 27 to control the degree of cooling provided thereby within interior chamber 4, such as by turning it off or turning it on. Based on the signal from humidity sensor 31, humidity control unit 19 controls the solenoid or other actuating mechanism for operating control valve 33 to increase or decrease the amount of moisture within interior chamber 4. Similarly, based on the signal from $CO_2$ sensor 37, $CO_2$ control unit 21 controls the solenoid or other actuating mechanism of control valve 39 in order to increase or decrease the amount of carbon dioxide entering interior chamber 4 in order to provide the appropriate level of $CO_2$ in accordance with the input settings. Fan assembly 23 may be operated to rotate the fan in order to gently blow the gas within interior chamber 4 to maintain a substantially uniform temperature, humidity and level of carbon dioxide throughout the chamber. Fan assembly 23 may be operated on a continuous basis or intermittently in a variety of predetermined patterns, which may be related to the opening and closing of door 5, especially to help recover the internal temperature and the $CO_2$ and humidity levels after the door has been opened and closed.

PCM 58 of the present invention helps to maintain interior chamber 4 at a substantially constant temperature due to the significant amount of latent heat which PCM 58 absorbs or releases during its phase change, namely melting or freezing. PCM 58 is especially helpful in maintaining that temperature if there is a loss of power to the heating element 29 or refrigeration assembly 28 for an extended period. More particularly, PCM 58 is configured to have a melting or freezing phase change temperature which is at or about a desired selected temperature of interior chamber 4. Thus, the storage item or items 40 may be placed in interior chamber 4 to help maintain the storage items near the phase change temperature of a given PCM 58 (block 161). Typically, the melting or freezing temperature of PCM 58 is within the range of about −40° C. (−40° F.) to about 150° C. (302° F.) or 160° C. (320° F.). However, the melting or freezing temperature of PCM 58 may be less or greater than this range.

In one embodiment, the melting temperature of PCM 58 is about 37° C. (98.6° F.) since this is one of the most commonly used temperatures for culturing bacteria and mammalian cells. One suitable phase change material which has a melting or freezing temperature of about 37° C. is available under the name "BioPCM Phase Change Material-37" from Phase Change Energy Solutions, Inc. of Asheboro, N.C. This product includes a phase change component and a fire suppression component. The phase change component is a derivative of fatty acids. The above noted business also produces PCMs which have respective melting or freezing temperatures anywhere within the range of about −40° C. to about 150° C. or 160° C. Similarly, phase change materials which are suitable for use as PCM 58 in the present invention are available from Entropy Solutions, Inc. of Minneapolis, Minn. Entropy Solutions, Inc. also produces a large variety of PCMs which have a respective melting temperature within the range of about −40° C. to about 150° C. or so. For example, one such PCM which melts or freezes at about 37° C. is available from Entropy Solutions, Inc. under the name "PureTemp 37." Likewise, Entropy Solutions, Inc. produces other PCMs, such as "PureTemp −40" having a melting point of about −40° C., "PureTemp −12" having a melting point of about −12° C., "PureTemp 4" having a melting point of about 4° C., "PureTemp 23" having a melting point of about 23° C., "PureTemp 30" having a melting temperature of about 30° C., "PureTemp 40" having a melting point of about 40° C. and "PureTemp 50" having a melting point of about 50° C. This company also produces a much wider variety of PCMs, for example PCMs (with analogous names) which have melting or freezing points respectively of about −14° C., about 7° C., about 15° C., about 18° C., about 27° C., about 30° C., about 43° C., about 48° C., about 53° C., about 55° C., about 56° C., about 61° C., about 68° C., about 103° C. and about 151° C. Entropy Solutions, Inc. is capable of producing a PCM of substantially any desired melting temperature. Entropy Solutions, Inc. indicates that the PCMs which they produce are from vegetable-based fats and oils. It is noted, however, that any suitable phase change material having the desired melting temperature may be used as PCM 58.

In some cases, it is desired to maintain the temperature of interior chamber 4 and item 40 at a temperature higher than room temperature (about 22 to 23° C. or 71 to 73° F.) or the ambient temperature, and thus PCM 58 is a solid at room temperature or at the ambient temperature. To take advantage of the phase change concept of such an embodiment of material 58, heating element 29 is operated in order to heat interior chamber 4 and the phase change material 58 until it melts at its melting phase change temperature (block 160). Most preferably, all of PCM 58 is melted so that PCM 58 is able to provide the greatest duration of substantially constant temperature during its phase change from the liquid state to the solid state while there may be no additional heat source available to maintain the interior temperature of interior chamber 4, such as during a power outage. In the heating scenario, each of the chambers positions the phase change material between the solid insulation and interior chamber 4, or positions the phase change material within interior chamber 4 itself so that insulation 56 of the container and the insulation of door 5A and/or the double paned window of door 5 substantially aids in preventing loss of heat from interior chamber 4.

In other cases, it is desired to maintain the temperature of interior chamber 4 and item 40 at a temperature lower than room temperature or the ambient temperature, and thus PCM 58 is a liquid at room temperature or at the ambient temperature. Thus, refrigeration assembly 28 is operated in order to cool interior chamber 4 and the phase change material 58 to its freezing point or phase change temperature so that it freezes or solidifies (block 160). Most preferably, all of PCM 58 is frozen or solidified so that PCM 58 is able to provide the greatest duration of substantially constant temperature during its phase change from the solid state to the liquid state while there may be no additional cooling or refrigeration source available to maintain the interior temperature of interior chamber 4, such as during a power outage. In the refrigeration scenario, the phase change material in the respective insulation chambers is positioned so that insulation 56 of the container and the insulation of door 5A and/or the double paned window of door 5 substantially aids in preventing the transfer of external heat into interior chamber 4. Although PCM 58 is well suited to help maintain the temperature during a power outage, it also helps in a variety of other situations. For instance, PCM 58 helps maintain and/or expedite recovery of the desired temperature within interior chamber 4 during and after door 5 is opened (FIG. 1) such as when item or items 40 are inserted and/or removed from interior chamber 4 (Arrows A in FIGS. 2, 5, 7-11, 13). Further, PCM 58 helps maintain or expedite recovery of the desired temperature when the temperature in chamber 4 is otherwise changed (increased or decreased) due to such factors as electrical power fluctuations, gas injections such as injection of carbon dioxide via $CO_2$ control unit 21, liquid injections such as injection of water via humidity control unit 19, exothermic or endothermic reactions occurring within item or items 40, and electronic devices which are part of an item 40. Such an electronic device might be, for example, lighting equipment such as might be used to simulate sunlight for growing plants, such that the light would produce heat when turned on within chamber 4. Another type of such an electronic device is a water pump for pumping water through an aqua tank, such as used for growing algae. Other examples of such an electronic device are a shaker for agitating a solution to facilitate growth, or a cell roller for rolling a bottle back and forth. Any of these electronic devices or others would during operation produce heat which would likewise tend to heat chamber 4 and any item therein. In addition, turning such electronic devices off while in chamber 4 would reduce the amount of heat energy that the electronic device produced within chamber 4 and thus alter the temperature in chamber 4. Likewise, altering the operation of such electronic devices in particular ways may also change the amount of heat that the device produces within chamber 4 at a given time. PCM 58 thus helps to maintain and/or facilitate recovery of the desired chamber 4 temperature in all of these scenarios or any other situation which would affect the internal temperature of chamber 4.

PCM 58 enhances the ability to maintain the stability of the temperature within chamber 4 as well as the uniformity of the temperature throughout chamber 4. The use of PCM 58 also enhances humidity uniformity in chamber 4 in combination with the humidity controls of the insulated chambers of the present invention, such that a stable dew point can be created in chamber 4, and the formation of condensation on items within chamber 4 or the walls defining chamber 4 can be minimized or eliminated. While the usefulness of PCM 58 has been described primarily as being related to its phase change characteristics, it is worth noting that PCM 58 also acts as an effective thermal mass and/or a thermal insulator.

It is also noted that other than PCM 58 and possibly the liquid medium 105, the other components of the various insulated chambers of the present invention are not considered to be PCMs, but rather remain in a single state, typically solid, throughout the entire range of the operational parameters of the given insulated chamber. Thus, among the components that remain in a solid state over the entire operational parameter of the insulated chambers of the present invention are the skins of the container and door, the control assembly, the various layers of insulation 70 and the like, the various control units, sensors and control valves, the heating and cooling devices (other than the liquid refrigerant within the cooling device), glass panes of the door where used, the seals used between the panes and between the door and the container, the wire or other similar shelves, the outer skin of the PCM packets, the fan assembly, the solid matrix when used, and any other components which would obviously remain in a solid state during the normal operational parameters of the insulated chamber.

Although the various insulated chambers described herein are similar, the certain aspects of the configurations may be more suited to certain purposes. For example, the upper and middle packets 84 in chamber 1B (FIG. 7) are positioned below and adjacent the respective shelf 2 and item 40 thereon, which is better suited for when the desired temperature of chamber 4 and item 40 is above the ambient temperature. On the other hand, the upper packet 84 in chamber 1C (FIG. 8) is positioned above and adjacent the upper shelf 2 and upper item 40 thereon, which is better suited for when the desired temperature of chamber 4 and item 40 is below the ambient temperature. Generally, the PCM is distributed strategically to enhance natural convection, and thus more PCM is located toward the bottom of chamber 4 when the desired chamber 4 temperature and PCM melting temperature is above the ambient temperature, whereas more PCM is located toward the top of chamber 4 when the desired chamber 4 temperature and PCM melting temperature is below the ambient temperature. In addition, more PCM is typically positioned adjacent the door opening to offset the heat loss path created in this area. It is further noted that various of the thermally conductive materials used in the present invention enhance thermal conduction between the PCM and interior chamber 4 and between the PCM and components within chamber 4 including item 40. In particular, layers 86 and 88 of packet 84 enhance such thermal conduction, as do inner layer 62 of skin 54 (FIGS. 2, 3) and inner layer 80 of skin 74 of door 5A (FIG. 5).

Figure 16:
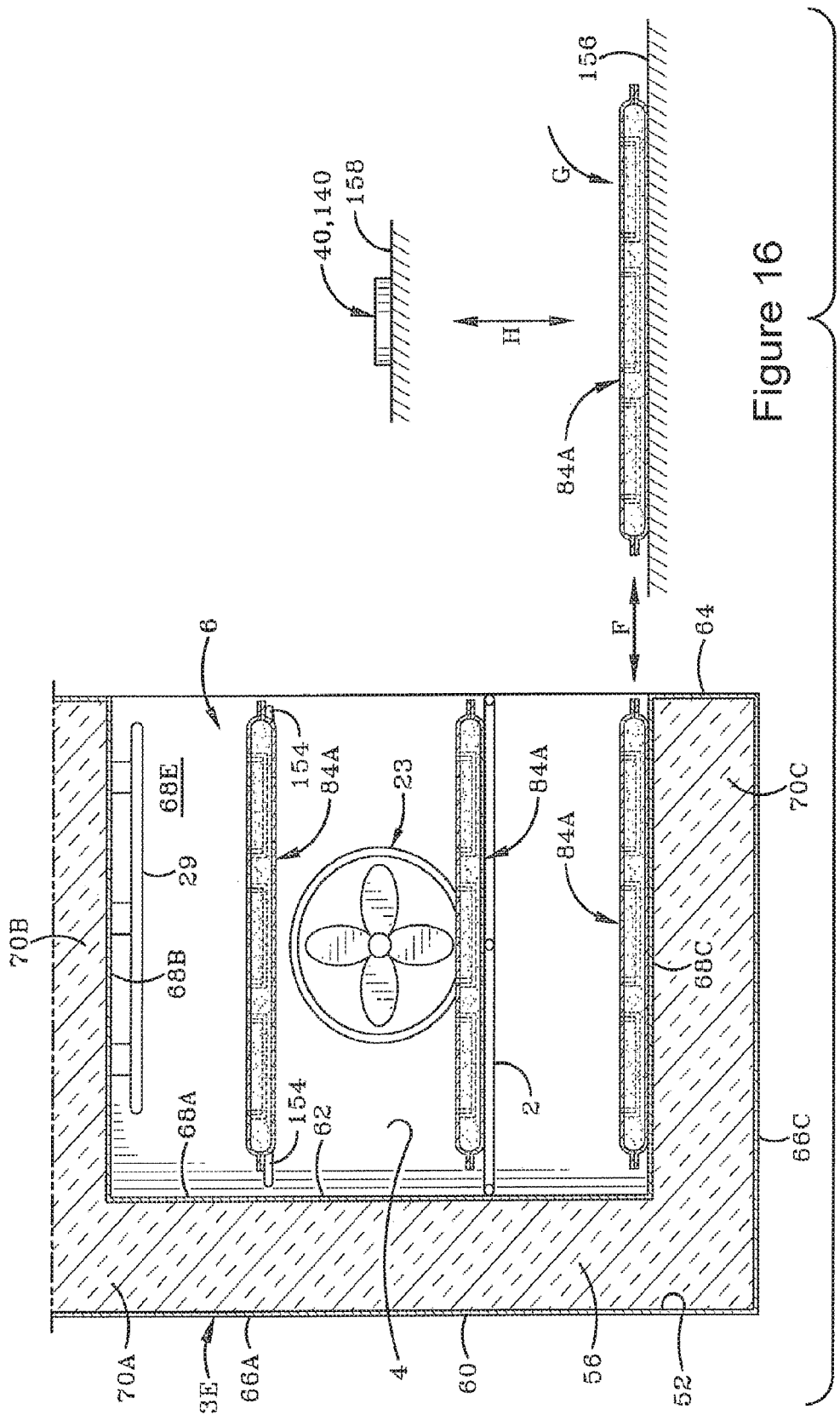
FIG. 16 is a sectional view similar to FIG. 15 with the door removed and portions cut away to illustrate the use of the PCM packets or shelves inside and outside of the chamber.

FIG. 16 illustrates an additional advantage of using packets or shelves 84A. More particularly, each shelf 84A is removable from and insertable into interior chamber 4 with items 40 thereon within recesses 128, as indicated at arrow F (block 161). Thus, a given packet 84A may be removed from interior chamber 4 and placed at a position outside the interior chamber 4 such as on a support surface 156 while the storage items 40, shown here as petri dishes 140, and the contents thereof, remain seated on the shelf within recesses 128 (block 163). While the storage items 40 and/or shelves 84A are removed from interior chamber 4, various procedures may be undertaken with regard to the storage items, either while the storage items are on or removed from the given shelf 84A or a similar shelf (block 164). Support surface 156 may, for example, be in the form of a table or a counter which is part of a fume hood whereby fumes from the petri dishes or other items under the hood may be exhausted. During the culturing of cells 152, it is necessary for the cells to be fed a suitable food, as indicated at arrow G. Thus, a worker may feed the cells 152 on medium 150 while the petri dish is seated within recesses 128 on packet 84A while the packet is on support surface 156 within a fume hood or the like. When the petri dishes are placed within recesses such as recesses 128, or remain seated atop a PCM packet like packet 84 in FIG. 6, the PCM of the corresponding packet helps to maintain the desired temperature of the item 40, including the medium 150 and cells 152 while they are outside the interior chamber 4 of insulated chamber 1H or the like. In addition, FIG. 16 illustrates that a given petri dish or other storage item 40 may be removed from the shelf or packet 84A when both are outside interior chamber 4 in order that the storage item 40 may be manipulated for other purposes. For example, storage item 40 may be removed from the packet (arrow H) and seated on another support surface 158. Support surface 158 also represents, for example, a scale on which item 40 may be weighed, or a microscope so that cells 152 or other components of item 40 may be viewed under the microscope. After a given item 40 has been manipulated on surface 158 or by any given tool as desired, it may be returned to the recess of packet 84 (arrow H) and other items 40 may similarly be removed and reinserted on packet 84. Once all procedures involving storage items 40 have been performed outside the insulated chamber, packet 84 with the various items 40 may be reinserted into interior chamber 4 (block 165).

Each of the chambers of the present invention may also be configured with two or more PCMs each of which has a different melting or freezing point. Thus, for example, one or more of layers 72A-E of chamber 1 (FIGS. 2-4) or layers 72A-F of chamber 1A (FIG. 5) may be formed of one PCM having a first melting or freezing phase change temperature while one or more of the other of said layers 72 may be formed of a PCM having a second melting or freezing phase change temperature which is different than the first melting or freezing temperature. Similarly, the layer 72G within one of packets 84 of chambers 1B or 1C (FIG. 7-8) may be formed of a PCM having the first melting or freezing temperature while another one of the layers 72G of the corresponding chamber 1B or 1C is formed of a PCM having the second melting or freezing temperature. Likewise, the layers 72A of chambers 1D or 1E (FIGS. 9-10) may have the first melting or freezing temperature while the respective layer 72B has the second melting or freezing temperature. Moreover, any one of the above noted PCM layers 72 may be formed of two or more different PCMs each having different melting temperatures. Whether these two or more PCMs are in separate layers or intermixed, the chamber thus provides the corresponding PCM for the respective first, second or third selected internal temperature of the interior chamber. In addition, the encapsulated pellets 104 of chambers 1F and 1G (FIGS. 11 and 13) may include two or more batches of pellets 104 such that the PCM 58 within one batch has a melting or freezing phase change temperature which is different than that of the other batch or batches. Configuring the chambers to have PCMs with differing melting or freezing temperatures may be useful, for example, in the pharmaceutical industry. In particular, drug manufacturers run stability tests on various medicines respectively at 30° C. and 40° C. (104° F.). Thus, the chambers of the present invention may be configured with one PCM having a melting point of about 30° C. and another PCM having a melting point of about 40° C. to facilitate maintaining the temperature of interior chamber 4 at the corresponding temperature as desired by the user. The melting or freezing phase change temperatures of the two PCMs in the above example are both, for example, above 0° C. and above the typical ambient temperature or typical room temperature of about 22° C. or 23° C. However, two or more PCMs used with a given insulated chamber of the present invention may also be configured to have melting or freezing phase change temperatures which are both below 0° C., the ambient temperature or the room temperature noted above, or may also be configured such that the phase change temperature of one of the PCMs is above one of these reference temperatures and the other is below the corresponding reference temperature.

Thus, where the chamber utilizes two phase change materials each having different melting or freezing phase change temperatures, the chamber may be operated to either heat or cool the first phase change material with one of the heating or cooling devices carried by the chamber to melt or freeze the first phase change material at its melting or freezing temperature while also heating or cooling the interior chamber to that temperature and incubating, storing or maintaining a given item within the interior chamber at about this first melting or freezing temperature. Subsequently, the chamber may be similarly operated to heat or cool the second phase change material and the interior chamber at a second melting or freezing phase change temperature of the second phase change material such that it melts or freezes. Then, either the item that was incubated, stored or maintained at the first temperature may also be incubated, stored or maintained at the second temperature (block 166), or it may be removed and another item may be inserted into interior chamber 4 (block 167) and incubated, stored or maintained at or near the second temperature (block 168). It is noted that the processes illustrated in FIG. 17 do not necessarily occur in the order shown nor are the processes necessarily separate as might be suggested by the arrows.

For optimum chamber thermal properties the PCM is disposed in all six sides (i.e., including the door such as the door 5 described above) of the chamber. As is known, the phase change material (PCM) is opaque when in a solid state and transparent when in a liquid state. Certain forms of PCM are packaged in opaque packets that are readily available, inexpensive, sealed, and made to accommodate thermal expansion without venting.

But if the PCM packaged in an opaque packet is placed in the chamber door, a user cannot see inside the chamber through the door, whether the PCM is in a liquid or solid form. Thus certain embodiments as described below place bulk PCM (i.e., not contained within opaque packet(s)) within the chamber door and control the PCM temperature to a liquid state and therefore transparent form. The primary reason for using PCM and placing it in all six chamber surfaces is to maintain the incubator internal temperature if an event, such as a power failure, occurs that would otherwise cause the internal temperature to change.

Also, the PCM functions most efficiently when its freezing/melting temperature is approximately the same as the desired incubator internal temperature. Therefore, for an incubator temperature of 37 degrees C. the preferred PCM has a melting temperature of 37 C. If a power failure occurs, the PCM returns or gives up its thermal energy by freezing (latent heat) and after freezing, by dropping in temperature (sensing heat).

However, placing PCM in the chamber door can be problematic. If the door does not contain a sufficient quantity of PCM, then the door is the weak link in maintaining the chamber internal temperature. And while the other five sides or walls of the incubator contain a sufficient amount of PCM to respond to temperature changes, the door may not.

Also, chamber users want to see into the incubator (through the door) without opening the door. The use of PCM in the form of opaque PCM packets in the door clearly prevents this.

The use of bulk PCM (not contained with a packet(s)) within the door and control of its temperature to change its physical state from a solid to a liquid would permit the user to see inside the chamber. But it may take up to about eight hours (e.g., overnight) for the PCM to completely melt to a transparent state. Clearly this is not an optimal solution.

Because of the lengthy time required to melt the PCM, generally, it is not a primary purpose of the door-based heater to change the state of the PCM. Instead its primary purpose is to assist with maintaining the interior chamber temperature and to provide optimal thermal storage by the PCM. It is clearly not practical to wait up to eight hours to change the PCM state and see inside the chamber.

One solution to this dilemma suggests a chamber with a double door. According to such an embodiment, the door comprises an outer solid door carrying the PCM (in the convenient packets and thus opaque) and an inner transparent (glass) door that maintains the chamber seal when the outer door is opened.

When a user desires to observe the contents of the chamber, he opens the outer PCM-based door and then can see into the chamber through the inner transparent door. The user can see inside the chamber without significantly affecting the stable temperature within the chamber.

More specifically, in that embodiment the material layers encountered as one proceeds from inside the chamber to outside the chamber through the inner and outer doors comprise: a hinged glass pane (the inner door), an air gap, a hinged first metal sheet, packetized PCM, a heater, an insulation layer, and a hinged second metal sheet. The two hinged metal sheets bound the outer door. For the user to view the interior chamber, she opens the outer PCM-based door and peers through the hinged glass pane.

But the two-door chamber design has certain disadvantages, including inconvenience and cost. Users prefer not to open two doors to gain access to a product in the chamber.

Thus certain embodiments of the present invention, as described below, comprise a single door (instead of the prior art two doors) through which users can see inside the chamber when desired, while also maximizing the quantity of PCM in the chamber by including bulk PCM within the door.

Figure 18:
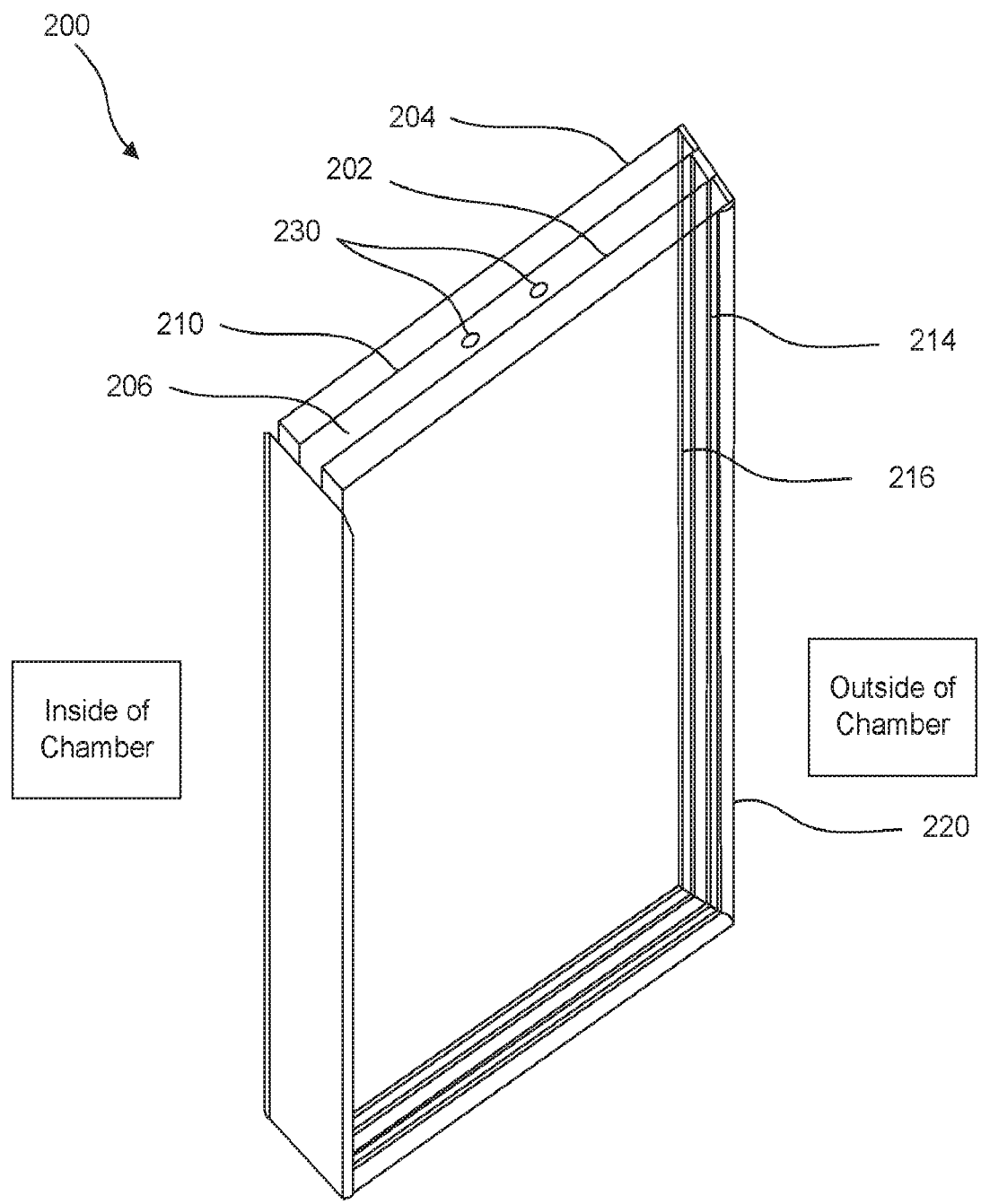
FIG. 18 is a perspective view of a two-pane chamber door with controllable transparency.

FIG. 18 illustrates such a single-door embodiment, comprising a chamber door 200 further comprising two transparent material panes 202, 204 (constructed from, for example, glass, Plexiglass® material of sheet, acrylic or another transparent material) with a cavity 206 between the panes filled with PCM 210.

In one embodiment of FIG. 18 the PCM 210 is not contained within an opaque packet, but is instead simply loaded into the cavity 206. It is thus referred to as bulk PCM herein.

A heater 214, for controlling the temperature of the PCM 210 (and therefore its physical state, either liquid or solid and further for controlling the interior chamber temperature) is depicted on an exterior-facing surface 216 of the transparent material pane 202, according to one embodiment of the door.

A frame 220 secures the panes 202, 204 and provides a liquid-tight seal for the PCM 210. Due to its thermal expansion, the PCM 210 either needs to be vented through vent openings 230 in the frame 220 (see FIG. 18) or a bladder (see a bladder 232 in FIG. 19) must be disposed within the cavity 206 to allow for that expansion and contraction.

Since the PCM 210 is sandwiched between two panes 202, 204, the PCM occupies a space with a fixed thickness and a fixed width. Any lateral expansion of the PCM in these directions is constrained by the panes 202, 204. But the depth or height of the PCM can vary based on the PCM temperature. The vent openings 230 or the bladder 232 accommodate this PCM thermal expansion.

Figure 19:
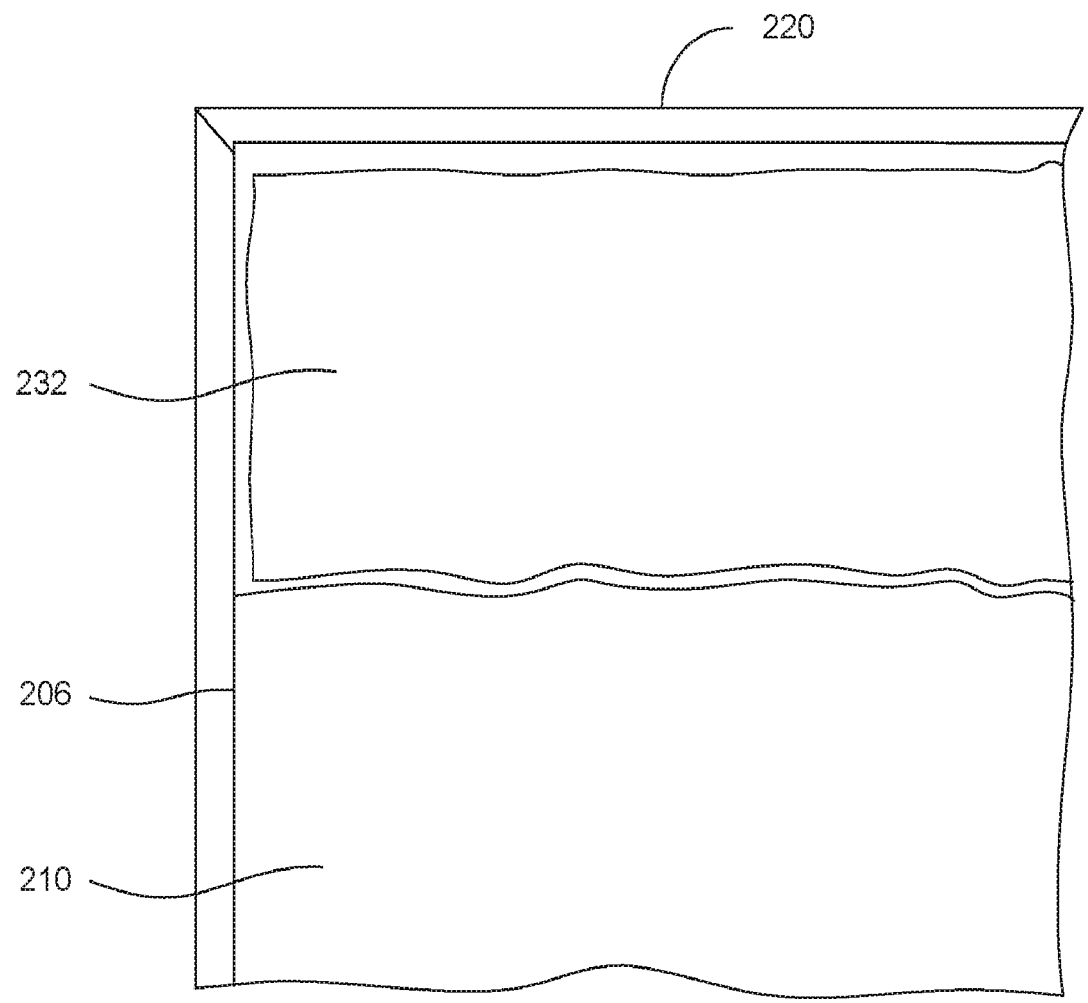
FIG. 19 is a close-up view of a region of a chamber door having a bladder disposed within the door.

FIG. 19 is a close-up view of the bladder 232 disposed in an upper and empty region of the cavity 206 above the PCM 210. Here the bladder 232 serves as a flexible lid for the PCM and the bladder itself must be air-tight to retain the air inside. However, the bladder may or may not provide a liquid-tight seal along a top surface of cavity 206 in which the PCM 210 is disposed. The bladder 232 may seal around interior surfaces of the frame 220. If the bladder 232 fails to provide such a seal, the frame 220 may provide the liquid-tight seal. But advantageously the bladder is flexible to deform vertically and laterally within the empty region of the cavity 206 as the PCM 210 expands or contracts.

Although in the embodiments of FIGS. 18 and 19 the PCM temperature can be controlled to change its physical state, this is not the primary purpose of the door-based heater nor may it even be a practical technique for changing the state of the PCM. In fact, as described above, it may take up to about eight hours for the PCM to completely melt to a transparent state. Instead, the purpose of the heater is to maintain the PCM at (or slightly above) a desired interior chamber temperature (37 degrees C., for example) to provide optimal thermal storage by the PCM.

The parenthetical reference above to maintaining the PCM at a temperature slightly above the desired interior chamber temperature is due to losses in the heat path from the PCM to the chamber INTERIOR. For example, the PCM heater may be maintained at 40 degrees C. and the proximate PCM is at a lower temperature, say 39 degrees C. The wall surface proximate the PCM is at a still lower temperature of 38 degrees C. and finally the chamber interior temperature is 37 degrees C.

Figure 20:
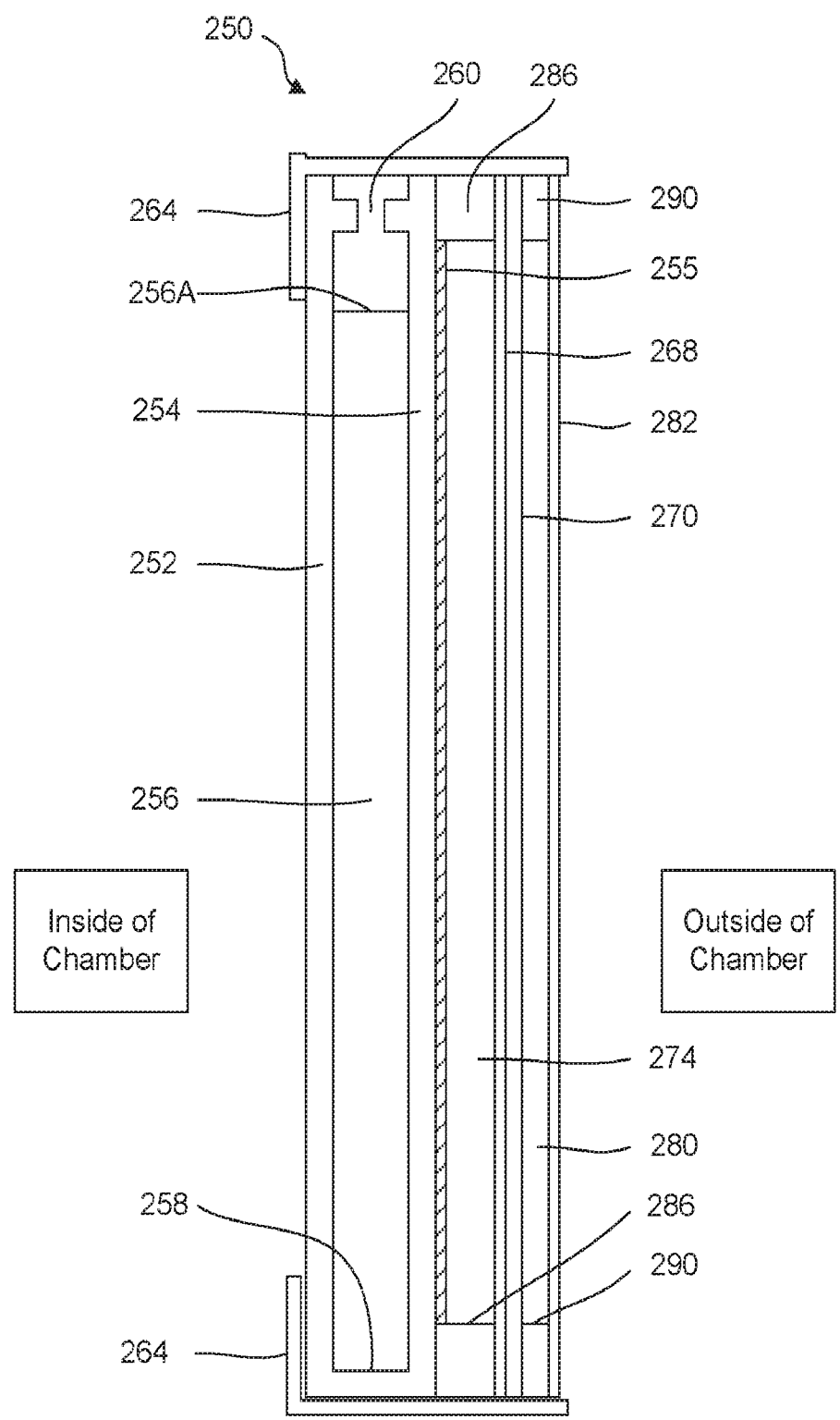
FIGS. 20 and 21 are top views of two four-pane door embodiments each with a controllably transparent pane.

Given the described disadvantage inherent in the door embodiments of FIGS. 18 and 19, the embodiment of FIG. 20 includes a controlled transparency material to obviate these disadvantages.

FIG. 20 illustrates a cross-sectional view of a preferred embodiment of an insulated chamber door 250 comprising two glass panes 252 and 254 with bulk PCM 256 disposed therebetween. A heater 255 is disposed in contact with or proximate to the glass pane 254. In another embodiment the heater 255 can be placed proximate the glass pane 252 or in contact with the PCM 256.

In this embodiment the PCM 256 is not contained within opaque packets or another opaque material. Here a bulk form of PCM is used and the temperature of the PCM 256 is controlled (primarily by the heater 255 and to a lesser extent by one or more heaters in the chamber wall(s)) to remain in a liquid/transparent state.

Certain door components are held together by spacers (comprised of glass, for example) 258 extending around the perimeter of the glass panes. An adhesive, such as epoxy, may be used to secure the glass spacers and glass panes together and create a liquid-tight seal, except for an air vent 260 disposed at the top of the assembly.

A metal (in one embodiment) door frame 264 extends around the perimeter of the door components and fixes them in place.

A top surface 256A of the PCM 256 extends upwardly to some distance below the air vent hole to allow for thermal expansion of the PCM.

In a preferred embodiment the door frame 264 comprises a sheet metal frame. But as is known by those skilled in the art, such a sheet metal frame is typically not air tight. Hence by design the frame will "breath" slightly, at least enough to provide a vent to the outside environment for the air vent 260 and thereby prevent pressure from building inside the frame.

The door 250 further comprises an acrylic pane 268 in contact with a smart glass material 270 (a controlled transparency material). A space between the glass pane 254 and the acrylic pane 268 forms an air gap 274.

Another air gap 280 is formed between an exterior acrylic pane 282 and the smart glass material 270.

The smart glass material 270 can comprise a controllable-transparency film applied directly to an acrylic pane (or alternatively applied to a glass pane), or a glass or acrylic pane with a smart glass film, or controllable-transparency material embedded therein, or a controllable-transparency material that is sprayed onto a glass or acrylic pane.

When current is applied to the smart glass the glass or film is activated to a transparent condition. Without the application of current the smart glass or film is opaque.

In the embodiment of FIG. 20 the smart glass material is applied to an acrylic pane due to door weight considerations. In another embodiment the smart glass material may be applied directly to a glass pane.

A door frame rubber (in one embodiment) spacer 286 is disposed between the acrylic pane 268 and the glass pane 254. A door frame rubber (in one embodiment) spacer 290 is disposed between the smart glass material 270 and the exterior acrylic panel 282.

Both the door frame spacers 286 and 290 and the door frame 264 extend around the perimeter of the door components.

While the PCM is maintained in a transparent/liquid form, controlling the smart glass material 270 to a transparent state allows the user to see inside the chamber.

In a simple embodiment a controller (not illustrated in FIG. 20 but see FIG. 21) comprises a user-operated switch to supply current to the smart glass and render it transparent whenever the user desires to see inside the chamber.

In another embodiment a time delay mechanism may be incorporated into the switch such that once closed, the switch opens after a selectable time interval.

In yet another embodiment the controller comprises two user-operated control settings. In a default mode the user simply touches the switch to render the smart glass transparent to enable viewing. Then after about 30 seconds, the smart glass automatically reverts to its opaque state.

According to another operational mode the user touches the switch to enable viewing. The smart glass remains transparent until the user touches the switch again to disable viewing.

In one embodiment the switch comprises a capacitive switch that does not require physical contact between the user's finger and the switch surface. The switch detects the user's finger (i.e., a body part) within a few millimeters and the switch changes state.

With reference again to FIG. 20, one embodiment of the present invention lacks the outer pane 282. In fact, the chamber door may comprise more or fewer than the illustrated four panes. Of course, with additional panes the door provides better thermal insulation. Additionally, if the panes are strategically placed relative to the door heater and the smart glass, the additional panes can isolate the door heater and the smart glass and provide a safer work environment for the user.

In one human cell culturing application employing a chamber with the door 250 of FIG. 20, the chamber is maintained at 37 degrees C. (or above) to provide optimal thermal PCM storage and maintain transparency (since the PCM 256 is a bulk form PCM).

Although the bulk PCM when in a transparent state provides visibility into the chamber, its important function is to maintain thermal stability within the chamber. The PCM can store a significant amount of thermal energy. But when the incubation chamber is subjected to a temperature disturbance, all the chamber PCM, obviously including the door-based PCM, functions to maintain the interior at 37 degrees C.

The most common potentially destructive temperature disturbance is a power failure. Without power the chamber cannot maintain the internal temperature and the PCM will instead release its thermal energy and thereby maintain the interior temperature. For example, without PCM surrounding an incubation chamber the interior temperature may fall by as much as 5 degrees C. in one hour. With a PCM layer in the incubator walls, the temperature may fall by 5 degrees C. in ten hours. The amount of PCM used in the chamber walls (including the door) dictates how long the chamber interior temperature can be maintained.

Another less problematic disturbance is opening of the chamber door.

Figure 21:
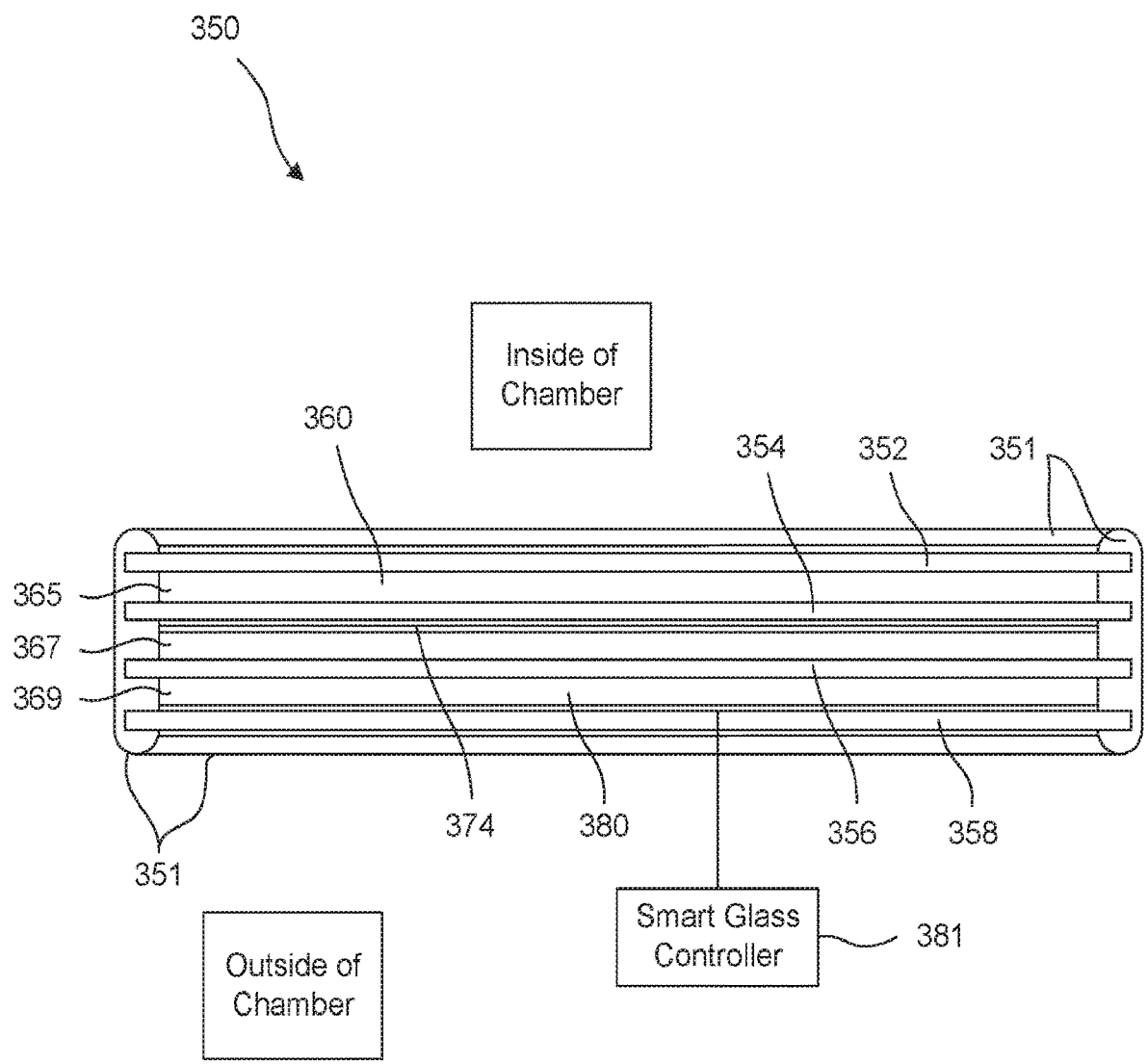

Another embodiment of the invention is depicted in a cross-sectional view of FIG. 21. A door 350 comprises a frame 351 supporting four panes of transparent material 352, 354, 356 358 with PCM 360 disposed within one or more of the gaps 365, 367, 369 formed between the four panes.

The door 350 further comprises a smart glass material layer or film 380 disposed on an interior-facing surface of the pane 358.

A heater is also disposed in one of the gaps, or on an interior-facing door surface, or on an exterior-facing door surface. Generally, it is desired to locate the heater toward the "outside" of the PCM 360. In the illustrated exemplary embodiment a heater 374 is disposed on the exterior-facing surface of the pane 354 and is proximate to the PCM 360.

Although it may be possible to use the heater disposed in one or more chamber sidewalls to control the transparency of the PCM in the door of the various presented embodiments, such may not always be preferred as a separate heater disposed on, in, or proximate the door (such as the heater 214 of FIG. 18, the heater 255 of FIG. 20, and the heater 374 of FIG. 21) may offer better control over the PCM in the door.

The door heater 214 (FIG. 18), 255 (FIG. 20) and 374 (FIG. 21) may be controlled by the chamber heater controller. The temperature of the door heater may be the same as or a proportional ratio of the chamber heater. According to one embodiment the door heater is connected to the chamber heater controller. However, in other embodiments the door heater is controlled separately from the chamber heater or can be switched to a 'manual' operational mode that provides a fixed percent 'on' control such as 50% on, or 75%, or 100%.

In any case, the door heater can melt the bulk PCM and thus can provide visibility into the chamber interior, albeit this may take several hours if the bulk PCM is not maintained in a transparent state. For example, the user may want to see inside the chamber on a schedule and thus if not maintained in a transparent state, activation of the PCM heater can be initiated to transform the PCM to a transparent state according to that schedule.

Thus according to at least the embodiments of FIGS. 20 and 21, control over the temperature (and therefore state) of the PCM and over the smart glass can be properly configured and coordinated to permit viewing inside the incubation chamber.

In the various presented embodiments with one or more air gaps, to provide additional insulation for the chamber, argon gas or air may be disposed in any of these gaps. It is known, however, that argon provides a higher R value, i.e., insulation value. Krypton may also be used to fill any of the gaps.

Generally, the smart glass material described herein can be disposed on any of the glass or acrylic surfaces of the various panes of the various embodiments. For example, the smart glass material can be applied to one of the transparent material panes 202 or 204 of FIG. 18.

Because smart glass requires an electrical current to operate, the inventors expect to locate the smart glass 'inside' the door layers where a user cannot physically touch the smart glass and experience a shock.

Similarly the heater (which may comprise a resistance heater) can be disposed between or on any of the glass or acrylic surfaces of the various embodiments. However, it is preferable to place the heater proximate the PCM to provide better temperature control over the PCM.

Yet another embodiment comprises a chamber door of three glass or acrylic panes. In one three-pane embodiment the smart glass is located on an interior-facing surface of an outer glass or acrylic pane. The bulk PCM and heater are preferably disposed in a proximate relation.

Although embodiments with two, three and four glass panes have been described, the chamber door can also be constructed with more than four glass panes.

One operating protocol of the present invention may maintain the door-based PCM in a transparent condition by maintaining the proper PCM temperature, while allowing the user to open or close the smart glass switch as desired to render the smart glass material opaque or transparent. Thus visibility into the chamber is achieved by simply closing the switch that controls the transparency of the smart glass.

Note that to change or hold the bulk PCM in the door in a transparent condition its temperature must be greater than the PCM in the chamber wall(s). This higher temperature in the door and its effect on the temperature in the chamber interior may need to be compensated by appropriately controlling the heater in the chamber wall(s). Thus more careful monitoring of the chamber interior temperature may be required to properly control the temperature of the heater in the chamber wall(s) to maintain the proper chamber temperature.

Certain of the embodiments described herein refer to PCM that melts/freezes at 37 degrees C., the human body temperature. Other embodiments and applications may use PCM with different compositions and therefore a different melting/freezing temperature. For example, when culturing fish cells, which tend to be cooler, PCM with a 37 degree C. melting temperature in the door will be opaque. Alternatively, if the user desires to maintain the door PCM in a transparent condition, a PCM with a different melting temperature must be used.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention is an example and the invention is not limited to the exact details shown or described.

What is claimed is:

1. A hinged door for gaining access to a chamber interior region for receiving a storage item therein, the hinged door comprising:
    a frame;
    a first transparent material pane within the frame;
    a smart glass material disposed proximate the first material pane, and controllable between a transparent and opaque condition responsive to an electric current supplied to the smart glass material;
    a first phase change material within the frame; and
    a first temperature controlling device proximate the first phase change material.

2. The hinged door of claim 1 the first phase change material disposed in a direction toward the chamber interior region relative to the first material pane, wherein the smart glass material is disposed in contact with an interior facing surface of the first material pane.

3. The hinged door of claim 1 further comprising a second material pane in a direction away from the chamber interior region relative to the first material pane, and wherein a material of the first and second material panes comprises one of glass, Plexiglass® sheet, and acrylic.

4. The hinged door of claim 1 further comprising a controller for controlling the electrical current supplied to the smart glass material.

5. The hinged door of claim 4 wherein upon activation of the controller by a user, the controller supplies electric current to the smart glass material for a predetermined time.

6. The hinged door of claim 4 wherein the controller comprises a time-delay mechanism for controlling electrical current flow to the smart glass material.

7. The hinged door of claim 1 further comprising:
    a second material pane in a direction away from the chamber interior region relative to the first material pane, and
    third and fourth spaced apart transparent material panes within the frame, the first phase change material disposed within a space defined between the third and fourth material panes, the third and fourth material panes in a direction toward the chamber interior region relative to the first material pane.

8. The hinged door of claim 7 wherein a material of the third and fourth material panes comprises glass.

9. The hinged door of claim 7 wherein beginning at the chamber interior, ordering of material panes comprises the fourth, third, first and second material panes, with a first air gap defined between the second and first material panes and a second air gap defined between the first and third material panes.

10. The hinged door of claim 7 further comprising a glass spacer disposed between the frame and aligned lower surfaces of the third and fourth material panes and the PCM.

11. The hinged door of claim 7 wherein an upper surface of the first phase change material is spaced apart from an inside surface of the frame to define a gap therebetween, the gap in fluid communication with an opening in the frame.

12. The hinged door of claim 7 for use with a chamber, the chamber comprising:
- a plurality of connected surfaces defining the chamber interior region;
- a second phase change material embedded in one of the plurality of surfaces; and
- a second temperature-controlling device for controlling a temperature of the second phase change material.

13. The hinged door of claim 1 wherein the first temperature controlling device controls a temperature of the first phase change material to maintain the first phase change material substantially in a liquid state.

14. An apparatus comprising:
- a closed container bounded by a plurality of surfaces defining an interior chamber region adapted to receive therein a storage item;
- a first phase change material embedded in one of the plurality of surfaces;
- a first temperature-controlling device within the storage interior or embedded in one of the plurality of surfaces for controlling a temperature of the first phase change material;
- a hinged door for gaining access to the storage interior chamber, the door further comprising:
  - a frame;
  - a first transparent material pane within the frame;
  - a smart glass material disposed proximate the first transparent material pane, responsive to an electric current the smart glass material assuming a transparent condition and in the absence of electric current the smart glass material assuming an opaque condition;
  - a second material pane disposed within the frame and spaced apart from the first material pane in a direction away from the interior chamber region, with the smart glass material on a surface of the first transparent material pane facing the second material pane;
  - the first and second material panes defining an air gap therebetween; and
  - third and fourth material panes and a second phase change material disposed therebetween, the third and fourth material panes spaced apart from the first material pane in a direction toward the interior chamber.

15. The apparatus of claim 14 further comprising a second temperature-controlling device capable of controlling a temperature of the second phase change material and maintaining the second phase change material substantially in a liquid state.

16. The apparatus of claim 14 wherein the closed container comprises an incubation chamber.

17. An apparatus comprising:
- a closed container bounded by a plurality of surfaces defining a storage interior chamber adapted to receive therein a storage item;
- a first phase change material embedded in one of the plurality of surfaces;
- a first temperature-controlling device embedded in one of the plurality of surfaces for controlling a temperature of the first phase change material;
- a hinged door for gaining access to the storage interior chamber, the door further comprising:
  - a frame;
  - first, second, third, and fourth parallel-oriented spaced-apart transparent material panes disposed within the frame, the first material pane bounding the storage interior chamber and the fourth material pane forming an exterior surface of the hinged door;
  - a second phase change material disposed between the first and second material panes;
  - a second temperature-controlling device disposed proximate the second phase change material;
  - a smart glass material disposed on one of the first, second, third and fourth material panes or between two spaced-apart panes, responsive to an electric current the smart glass material assuming a transparent condition and in the absence of electric current the smart glass material assuming an opaque condition; and
- a controller for controlling electrical current flow into the smart glass material.

18. The apparatus of claim 17 the smart glass material disposed on an exterior facing surface of the third material pane.

* * * * *